(12) United States Patent
Coveley et al.

(10) Patent No.: US 7,817,046 B2
(45) Date of Patent: Oct. 19, 2010

(54) METHOD AND APPARATUS FOR CATALOGING AND POLING MOVEMENT IN AN ENVIRONMENT FOR PURPOSES OF TRACKING AND/OR CONTAINMENT OF INFECTIOUS DISEASES

(75) Inventors: Michael Coveley, Richmond Hill (CA); Yuping Huang, Richmond Hill (CA)

(73) Assignee: Cstar Technologies Inc., Toronto, Ontario (CA)

( * ) Notice: Subject to any disclaimer, the term of this patent is extended or adjusted under 35 U.S.C. 154(b) by 840 days.

(21) Appl. No.: 10/589,128

(22) PCT Filed: Feb. 11, 2005

(86) PCT No.: PCT/CA2005/000175
§ 371 (c)(1),
(2), (4) Date: May 1, 2007

(87) PCT Pub. No.: WO2005/079122
PCT Pub. Date: Aug. 25, 2005

(65) Prior Publication Data
US 2007/0222599 A1   Sep. 27, 2007

Related U.S. Application Data

(60) Provisional application No. 60/543,327, filed on Feb. 11, 2004.

(51) Int. Cl.
*G08B 23/00* (2006.01)

(52) U.S. Cl. ............ 340/573.1; 340/572.1; 340/539.12; 340/539.13

(58) Field of Classification Search ............ 340/573.1, 340/572.1, 572.7, 10.1, 539.1–539.13
See application file for complete search history.

(56) References Cited

U.S. PATENT DOCUMENTS

| | | | |
|---|---|---|---|
| 6,052,062 A | 4/2000 | Tuttle | |
| 6,456,239 B1 | 9/2002 | Werb et al. | |
| 6,483,427 B1 | 11/2002 | Werb | |
| 7,394,370 B2* | 7/2008 | Chan | 340/572.1 |
| 2005/0248438 A1* | 11/2005 | Hughes et al. | 340/10.4 |
| 2007/0257857 A1* | 11/2007 | Marino et al. | 343/867 |

FOREIGN PATENT DOCUMENTS

| | | |
|---|---|---|
| CA | 1295717 | 2/1992 |
| CA | 2 481 353 | 10/2003 |

OTHER PUBLICATIONS

JISC RFID: Frequency, standards, adoption and innovation, May 2006, Ward.*

* cited by examiner

*Primary Examiner*—Jeffery Hofsass
(74) *Attorney, Agent, or Firm*—Volpe and Koenig P.C.

(57) ABSTRACT

A system and method for containing and restricting spread of infectious diseases within hospitals, clinics and other medical facilities by cataloguing and delimiting movement of patients, medical staff, employees, visitors, contractors and other personnel attending or on-site. The system also provides for tracking and cataloguing contaminated medical apparatus, medicine trolleys, food trolleys, medical gas stations, laundry baskets and other mobile or movable medical equipment or facility equipment to prevent spread of the infectious disease or viral entities. According to another aspect, the system includes a poling or supervisory network for auditing the presence or absence of patients, medical staff and other personnel; and medical apparatus, movable equipment or other facility equipment.

11 Claims, 18 Drawing Sheets

METHOD AND APPARATUS FOR CATALOGING AND POLING MOVEMENT IN AN ENVIRONMENT FOR PURPOSES OF TRACKING AND/OR CONTAINMENT OF INFECTIOUS DISEASES

FIELD OF THE INVENTION

The present invention relates to a method and apparatus for tracking and poling the movement of people and equipment and articles in a defined environment for the purposes of containment of infectious diseases and other contagion.

BACKGROUND OF THE INVENTION

Recent outbreaks of critically dangerous and acute infectious diseases have demonstrated how rapidly diseases can be spread before health authorities and other governmental agencies are able to identify and establish an outbreak state. Once an outbreak has occurred, containment becomes a priority and typically involves tracking the infected individuals back to the source.

As illustrated by the SARS outbreak, identifying individuals who have been exposed to the infectious virus or disease and then tracking the exposure of these individuals become the critical criteria in containing the further spread of the disease.

Accordingly, there remains a need for a system and procedures for tracking and delimiting movement of people and equipment in a defined environment in order to quickly contain infectious diseases.

BRIEF SUMMARY OF THE INVENTION

The present invention provides a method and apparatus for tracking, cataloguing and/or delimiting movement in an environment for the purposes of containing infectious diseases or other contagion. In another aspect, the present invention provides a method and apparatus for poling and providing a supervisory function for identified personnel and devices or equipment within the environment.

According to one aspect, the present invention provides a process for cataloguing and delimiting movement of patients, medical staff, employees, visitors, medical equipment, medicine trolleys, food trolleys, medical gases, laundry hampers, and other equipment or personnel in a healthcare environment, for example, a hospital, a medical center, or a smaller facility, such as a clinic or a doctor's office. In accordance with this aspect, tracking mechanisms are provided for tracking, cataloguing and delimiting the movement within the environment.

According to another aspect, the tracking, cataloguing and delimiting procedure operates on two levels. The first level comprises operation during normal conditions in a healthcare facility, for example, a hospital or a doctors' clinic. The second level comprises operation during an outbreak of an infectious disease or a contagious state.

The system comprises electronic tagging components and tracking components. The electronic tagging components are coupled or affixed to personnel in the facility on entering the facility and also to medical equipment and other apparatus which may be moved around the facility or into or out of the facility.

During normal conditions, the system operates at a first level to allow normal procedures to subsist for patients, hospital medical staff, visiting medical staff, visitors, general public entering the facility and contractors visiting or working in the facility. Operation at this level allows movement of personnel and equipment and apparatus to be observed and recorded. Information regarding the recorded movement is available for archive for future reference.

During an infectious outbreak or other alert state, the system operates at a second level with immediate access to recorded data and newly collected information on movement of personnel and equipment into and throughout the facility in order to facilitate or assist in tracking and containing potential carriers of the infectious contagion.

In one embodiment, the present invention provides a system for providing containment of an infectious disease in a facility, the system comprises: one or more of scrutinizers, each of the scrutinizers includes a receiver for receiving an identification signal, and further includes an output module for outputting a signal in response to the identification signal being received; one or more identification tags, one of the identification tags being worn by each person having entry in the facility, and each of the identification tags including a transmitter for transmitting the identification signal associated with the person wearing the respective identification tag; the scrutinizers being located throughout the facility including an entrance scrutinizer, an exit scrutinizer, and one or more passageway scrutinizers; a controller, the controller having an input port for receiving the output signals generated by each of the scrutinizers, and further including a processing module, the processing module having a sub-module for creating a record for each of the persons having entry in the facility, the record including temporal information from one or more of the scrutinizers having detected the identification signal associated with the person.

In another embodiment, the present invention provides a method for tracking potential carriers of an infectious disease in a facility, the method comprises the steps of: assigning a unique identifier to each individual having access to the facility, and providing each of the individuals with a transmitter for transmitting the assigned unique identifier; detecting transmission of the unique identifiers for the individuals at one or more locations in the facility based on movement of the individuals; establishing a record for each the individuals, each of the records including temporal data indicating time and date for detection of the unique identifier for the associated individual; storing the records and making the records available for retrieval; identifying one or more of the individuals as the potential carriers; retrieving the records associated with each of the identified individuals; establishing an area of movement for each of the identified individuals, the area of movement being based on the temporal data and the locations in the facility where the unique identifier was detected.

In yet another embodiment, the present invention provides a system for tracking the movement of persons in a facility as potential carriers of an infectious virus or disease, the system comprises: one or more receivers, each of the receivers having an input for receiving an identification signal, each of the persons in the facility having an associated identification signal, and each of the receivers including an output for outputting an output signal for each of the identification signals; one or more transmitters, each of the persons wearing one of the transmitters, and each of the transmitters transmitting the identification signal associated with the person; the receivers being located throughout the facility; a controller having an input port for receiving the output signals, and including a component for generating a temporal record for each of the persons in response to the detection of the identification signal of the person by one or more of the receivers.

In a further aspect, the present invention provides a system for tracking and auditing the movement of persons in a facility, the system comprises: a first network having a plurality of receivers, each of the receivers includes an input for receiving an identification signal, each of the persons in the facility have an associated identification signal, and each of said receivers includes an output for outputting an output signal for each of said identification signals; a plurality of transmitters, each of the persons wear one of the transmitters, and each of the transmitters transmits the identification signal associated with the person; a plurality of receivers are located throughout the facility; a controller having an input port for receiving the output signals, and including a component for generating a temporal record for each of the persons in response to the detection of the identification signal of the person by one or more of the receivers; a second network having a plurality of transceivers, each of the transceivers includes a poling transmitter for transmitting a poling request to the transmitters, and each of the transceivers includes a poling receiver for receiving identification signals in response to the poling requests; and the controller further includes an interface for receiving the poled identification signals, and includes a component for generating an audit record for each of the transmitters in response to said poling request.

In yet another aspect, the present invention provides an identification apparatus for use with a system for tracking the movement of persons in a facility, the identification tag comprises: a carrier member having a first surface; a passive antenna; an active antenna; the passive antenna comprises one or more windings mounted on the first surface in proximity to the periphery of the carrier member; the active antenna comprises one or more windings mounted on the first surface and within the periphery of the windings for the passive antenna; a receiver circuit; a transmitter circuit; and the receiver and the transmitter circuits are electronically coupled to the passive and the active antennas.

In a further embodiment, the present invention provides a method for tracking and auditing the movement of persons in a facility, the method comprises the steps of: assigning an identifier to each person having access to the facility, and providing each of the persons with a transmitter for transmitting the assigned identifier; detecting transmission of the identifiers for the persons at one or more locations in the facility based on movement of the persons; establishing a record for each of the persons, each of the records including temporal data indicating time and date for detection of the identifier for the associated person; storing the records and making the records available for retrieval; poling the transmitters by sending one or more poling requests to one or more of the transmitters; receiving identification signals from the transmitters in response to the poling request; generating an audit record for the transmitters based on the identification signal received in response to the poling request.

Other aspects and functions of the present invention will become apparent to those ordinarily skilled in the art upon review of the following description of specific embodiments of the invention in conjunction with the accompanying drawings.

BRIEF DESCRIPTION OF THE DRAWINGS

Reference will now be made, by way of example, to the following drawings which show, by way of example, embodiments of the present invention, and which.

DETAILED DESCRIPTION OF EMBODIMENTS OF THE INVENTION

Figure 1:
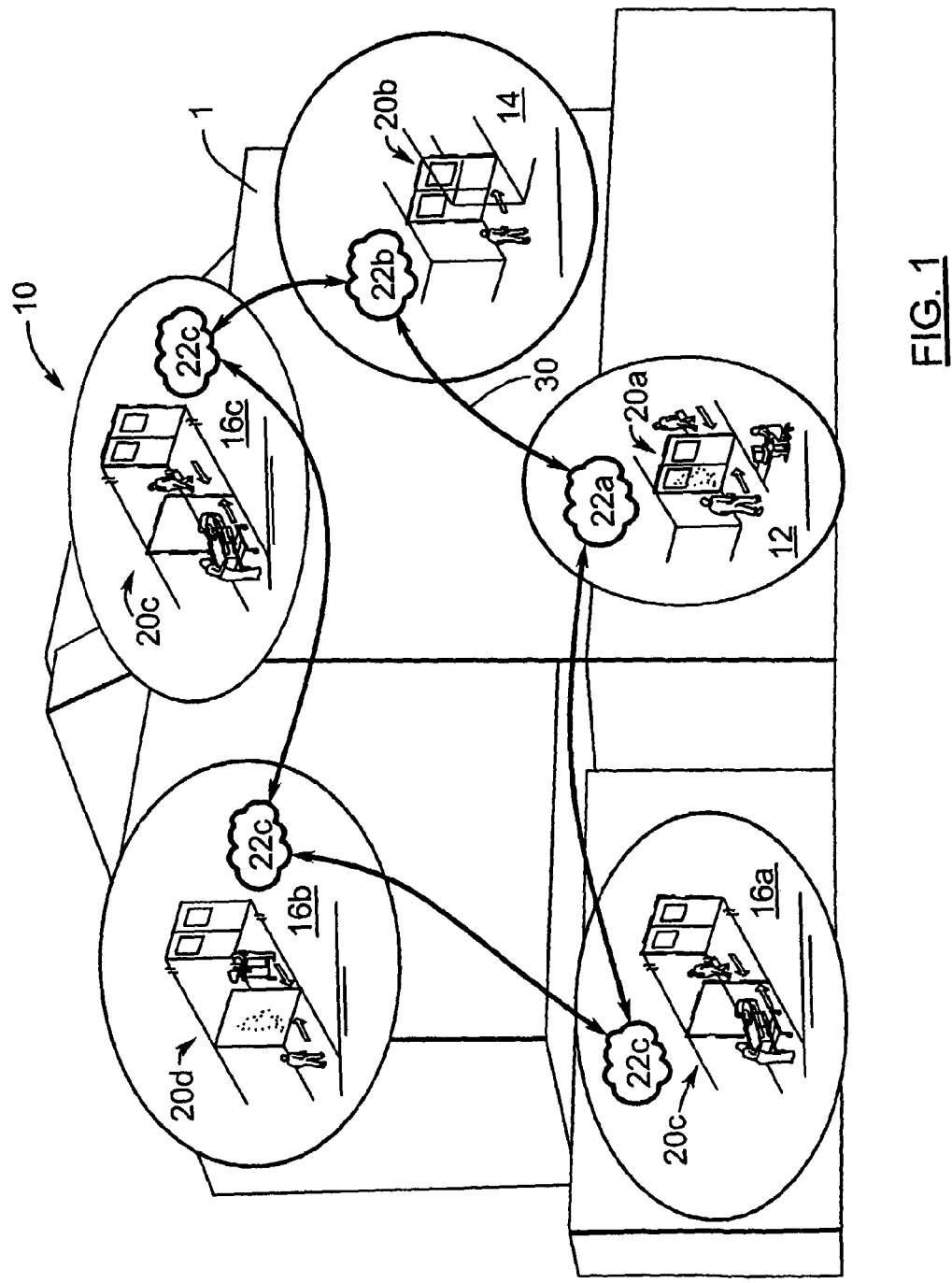
FIG. 1 is a schematic diagram showing an exemplary healthcare facility configured with a system for tracking and scrutinizing movement scrutinizer and a cataloguing mechanism in accordance with the present invention.

Reference is first made to FIG. 1, which shows in diagrammatic form a healthcare facility configured With a system 10 according to the present invention. The healthcare facility denoted generally by reference 1 comprises a hospital, medical centre, doctors' clinic or other similar type of building or complex. While the present invention is described in the context of a multi-floor healthcare facility, it is to be appreciated that the system is equally applicable to larger complexes, or to smaller buildings, for example, a walk-in health clinic or a doctor's office.

While the system 10 and processes according to the present invention are described in the context of hospitals, and medical facilities in general, it is to be appreciated that the present invention has wider applicability to passenger terminals, such as airports, train terminals and bus depots; public meeting or gathering places, such as shopping malls, cinemas, theatres and hotels; governmental facilities, such as military headquarters, military bases, military research facilities, government offices; prisons; schools and universities; theme parks; and shipping vessels. In addition, the system 10 is suitably configurable, for example via a wide area network, to a complex with multiple buildings or sites, for example, hospitals belonging to a healthcare network, or military hospitals or healthcare facilities for the armed forces or a division of the forces. The wide area network may be based on a private or proprietary architecture, or a public or open source architecture, such as the Internet, for example, operating with an encrypted or secure layer or layers.

As shown in FIG. 1, a system for tracking, cataloguing and delimiting movement of personnel and apparatus 10 in a healthcare facility 1 comprises a number of tracking stations 20, a network 30, and a control module 40. The tracking stations 20 are indicated individually by references 20a, 20b, 20c, 20d and 20e. Each of the tracking stations 20 is installed at an entrance point 12, and exit point 14, or a traffic or movement corridor or passage 16 in the healthcare facility 1 or other traffic or movement scrutinizing location. As shown in FIG. 1, the tracking system 20a is configured for the entrance point 12 (for example, the front door or main entrance and reception area), the tracking station 20b is installed for the exit 14 (for example, the emergency exit), the tracking station 20c is installed in a first floor passage corridor 16a, the tracking station 16b is installed in a second floor passage corridor 16b, and the tracking station 16c is installed for an upper floor passage corridor 16c. The tracking stations 20 each include a network component 22, indicated individually as 22a, 22b and 22c in FIG. 1. The network components 22 are coupled together to form the network 30. As will be described in more detail below, the network 30 comprises a (wireless) local area network 100 (FIG. 8) or LAN, a wide area network or WAN, or the Internet. The network 30 may be based on a generally available architecture or a proprietary architecture.

The tracking stations 20 are configured in the entrance way 12, the exit point 12 and in the corridors 16. In a typical healthcare facility 1, the corridors 16 for installing the tracking stations 20 are selected based on a number of factors, including: amount of traffic (e.g. high traffic passages), special purpose corridors (e.g. emergency room), function specific areas (e.g. intensive care unit, surgery, medicine dispensary, food services, laundry services, heating and cooling control), maintenance corridors or passage ways, restricted access passage ways, or passage ways leading to construction areas. The network capability of the tracking stations 20 allows additional stations 20 to be installed and/or the system 10 to be reconfigured or rearranged according to physical or traffic pattern changes in the facility 1.

Figure 2:
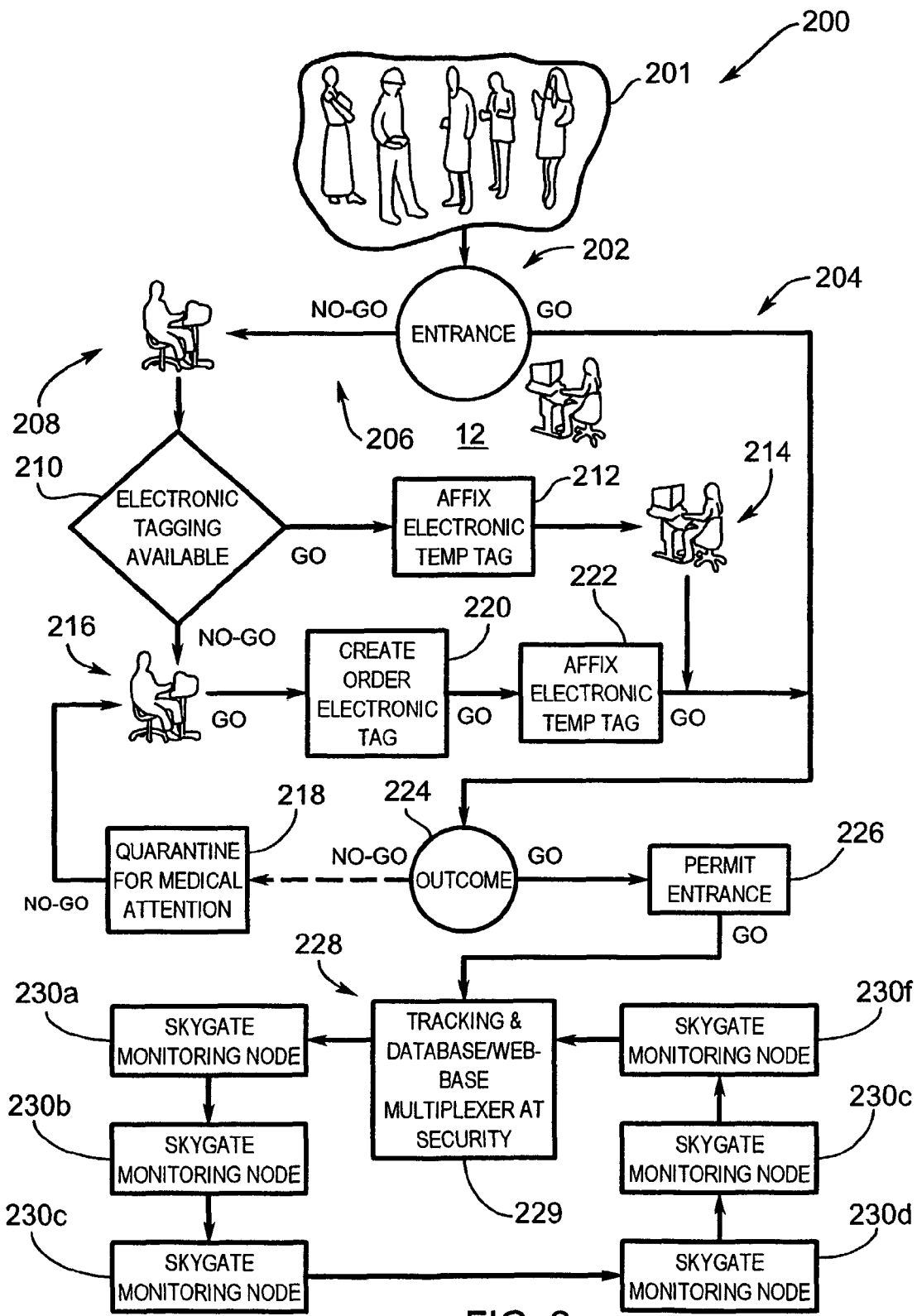
FIG. 2 shows in flow-chart form a procedure for cataloguing and delimiting movement of personnel and apparatus in a healthcare facility during normal conditions.

Reference is next made to FIG. 2 which shows in flowchart form a cataloguing and delimiting procedure in accordance with the present invention and indicated generally by reference 200. The cataloguing and delimiting procedure 200 is configured for the healthcare facility 1 operating under normal conditions or in healthful times i.e. without a contagious disease outbreak or infectious condition. According to this aspect, the system 10 continues to perform monitoring and recording or cataloguing functions because an outbreak is not usually predictable. In the event of an infectious disease outbreak or contagious condition, the system 10 changes in operation to a high scrutiny level as will be described in more detail below and also with reference to FIG. 3. Data collected or catalogued during healthful times is made available in order to assist in tracing or establishing possible conditions or states leading to the outbreak.

As shown in FIG. 2, the cataloguing and delimiting procedure 200 comprises a scrutinization operation indicated by reference 202. Personnel attending the facility 1 include medical staff, patients, visitors and may also include contractors. The personnel are indicated generally by reference 201. The scrutinization operation 202 is performed in the main entrance corridor or reception area 12, and comprises scrutinizing personnel entering or attending the facility 1. Personnel 201 are differentiated as regular, and as unusual, and with electronic tags. Regular personnel with electronic tags are allowed into the facility 1 as indicated by 204. Unusual or non-typical personnel are subjected to further scrutiny as indicated by 206. As indicated by 208, the unusual personnel are allocated an identification number, which may comprise their social insurance number (SIN) or their social security number (SSN) or other identifier which is unique to a person. (According to another aspect, a RFID tag may be encapsulated into the SIN or SSN identifier or card.) The identifier is used to retrieve information from a database to determine if the person has been exposed to a disease or is suffering a condition which would necessitate limiting or preventing access to the facility 1. Next a decision is made in block 210 to determine if electronic tagging is allowed. If allowed, a temporary electronic tag is affixed to the personnel 212. This may be followed by an interview stage as indicated by reference 214. If electronic tagging is not allowed (as determined in step 210), then the personnel are subjected to an interview in step 216. If it is determined that the subject personnel has been exposed to an infectious disease, is exhibiting symptoms of a disease or infection or should otherwise be observed, then the personnel is not issued a temporary electronic tag and directed to quarantine for medical observation or attention as indicated by reference 218. Following the interview stage 214, affixing of a temporary electronic tag 222 or entry as regular personnel with an electronic tag 204, another screening step is performed in step 224. If the screened personnel are clear to enter based on interrogation of the affixed electronic tag or temporary electronic tag and retrieval of information from the database, then entrance into the facility 1 is permitted in step 226. If the personnel screened in step 224 are not permitted entrance, they are directed to quarantine for further medical observation in step 218.

Once admitted to the facility 1, personnel with an electronic tag or a temporary electronic tag are tracked using apparatus installed or located throughout the facility 1. As indicated by reference 228, the movement of personnel is tracked and stored in a database 229. Movement of personnel is tracked using monitoring nodes located throughout the facility 1 in corridors and portals indicated individually as 230a, 230b, 230c, 230d, 230e and 230f. The monitoring nodes 230 (for example, the tracking stations 20 in FIG. 1) are coupled together to form a local area network 232 with the database 229. Records concerning the movement of personnel throughout the facility 1 are generated and stored in the database 229. The database 229 and other monitoring and scrutinizing equipment may be located in a central location in the facility 1, such as the information technology center or security office. The records may also be transmitted, e.g. emailed, to a central health authority.

Figure 3:
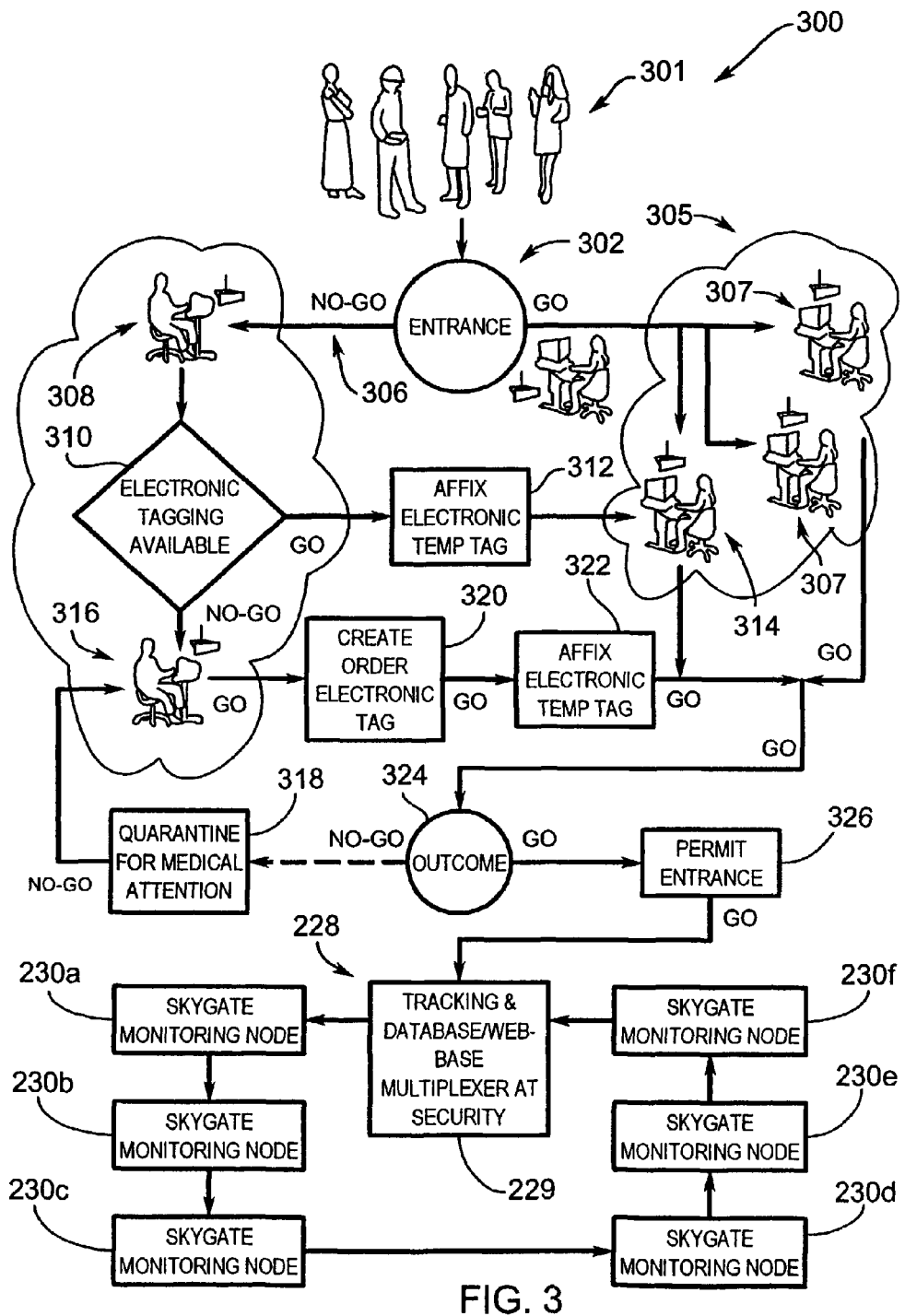
FIG. 3 shows in flow-chart form a procedure for cataloguing and delimiting movement of personnel and apparatus in a healthcare facility during an outbreak state.

Reference is next made to FIG. 3, which shows in flowchart form a tracking or cataloguing and delimiting procedure for unhealthful times in accordance with the present invention and indicated generally by reference 300. The cataloguing and delimiting procedure 300 is configured for the healthcare facility 1 operating under infectious conditions or unhealthful times i.e. a contagious disease outbreak or infectious condition. According to this aspect, the system 10 performs additional monitoring and scrutinization functions as compared to the tracking or cataloguing and delimiting procedure 200 described above with reference to FIG. 2.

As shown in FIG. 3, the cataloguing and delimiting procedure for unhealthful times, indicated generally by reference 300, comprises a scrutinization operation indicated by reference 302. As described above, personnel attending the facility 1 include medical staff, patients, visitors and may also include contractors and are indicated generally by reference 301 in FIG. 3. The scrutinization operation 302 is performed in the entrance corridor or reception area 12, and comprises scrutinizing personnel entering or attending the facility 1. Personnel 301 are differentiated as regular, and as unusual, and with electronic tags. As will be described in more detail below, under the procedure 300 for unhealthful times, all personnel and traffic 301, included both regular electronic tagged traffic 304 and unusual non-electronic tagged traffic 306, are subjected to greater scrutiny.

Referring to FIG. 3, the unusual or non-typical personnel 306 are subjected to scrutiny as indicated by reference 308. The unusual personnel are allocated an identification number, which may comprise their social insurance number (SIN) or their social security number (SSN) or other identifier which is unique to a person. The identifier is used to retrieve information from a database to determine, for example, if the person has been exposed to a disease or is suffering a condition which would necessitate limiting or preventing access to the facility 1. Next a decision is made in block 310 to determine if electronic tagging is available in a manner similar to that described above with reference to FIG. 2. If available, a temporary electronic tag is affixed to the personnel 306 in block 312. This is followed by an interview stage as indicated by reference 314. If electronic tagging is not available (as determined in step 310), then the personnel are subjected to an interview in step 316. If it is determined that the subject personnel has been exposed to an infectious disease, is exhibiting symptoms of a disease or infection, or should otherwise be observed, then the personnel is not issued a temporary electronic tag and directed to quarantine for medical attention as indicated by reference 318. If the subject personnel pass or complete the interview at 316, then an order for an electronic tag is created in block 320, and a temporary electronic tag is affixed to the subject personnel in block 322.

Referring to FIG. 3, regular personnel 301 with electronic tags enter the facility 1 at an entrance indicated by 302. At the entrance 302, the electronic tags worn by the regular personnel are scanned by apparatus (as described in more detail below), and based on the scanning operation the personnel are admitted as regular electronic tagged traffic indicated by reference 304. The scanning operation comprises reviewing database records associated with the regular personnel to determine if they present an infection risk, for example, if the regular personnel have been exposed or if showing symptoms. Database records and other information are retrieved using the unique identifier association. However as compared to the procedure 200 in FIG. 2, the regular electronic tagged personnel 304 are subjected to further scrutiny indicated by reference 305. During unhealthful times, the regular tagged personnel 304 are subjected to an interview as indicated by reference 314. The further scrutiny 305 may also comprise travel interview scrutiny. As shown in FIG. 3, a domestic interview stage 307 and an overseas or international travel interview stage 309 are provided. The domestic interview stage 307 provides screening and information collection for personnel who have travelled domestically, but may have been exposed. The overseas travel interview stage 309 provides screening and data for personnel who have travelled internationally or overseas. The purpose of the interview stages 307 and 309 is determine if the personnel have been exposed or infected as a result of their travel. The collected information and data are stored in the database and may be used to establish and/or track a breakout or exposure history for a contagious disease or virus. For example, one or more of the regular personnel 304 may have been subjected to an infectious disease or contagion while travelling and according to this aspect, it is desirable to detect or screen such personnel 304. Information or data collected during the interview 314 or travel interview 305 is stored in the database, and archived and/or compiled for subsequent screening and decision making.

Following the interview stage 314, affixing of a temporary electronic tag 322 or interview 314 or travel interview 305 as regular personnel 304 with an electronic tag, another screening step is performed in step 324. If the screened personnel are clear to enter based on interrogation of the affixed electronic tag or temporary electronic tag and on scrutiny of information retrieved from the database, then entrance into the facility 1 is permitted in step 326. If the personnel screened in step 324 are not permitted entrance, they are directed to quarantine for further medical observation or attention in step 318. Once admitted to the healthcare facility 1, personnel with an electronic tag 304 or personnel 306 with a temporary electronic tag are tracked using apparatus (i.e. the tracking and scrutinizing stations 20 in FIG. 1) installed or located throughout the facility 1. As indicated by reference 228, the movement of personnel 304, 306 is tracked and stored in a database 229. Movement of personnel is tracked using monitoring nodes located throughout the facility 1 in corridors and portals indicated individually as 230a, 230b, 230c, 230d, 230e and 230f. The monitoring nodes 230 are coupled together to form a local area network 232 with the database 229. Records concerning the movement of personnel 304, 306 throughout the facility 1 are generated and stored in the database 229. The database 229 and other monitoring equipment may be located in a central location in the facility 1, such as the security office.

Figure 4:
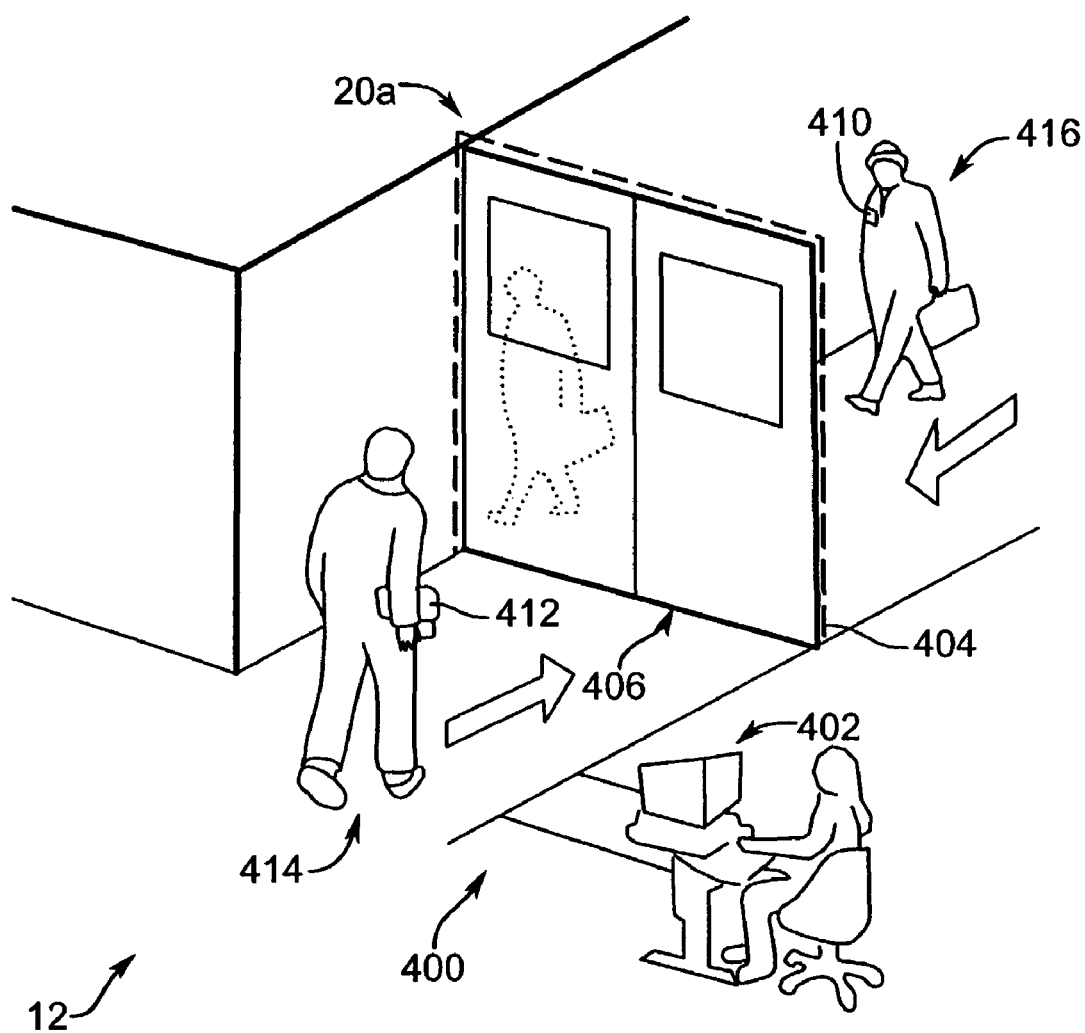
FIG. 4 shows an access and security scrutinizer for the facility of FIGS. 2 and 3.

Reference is next made to FIG. 4, which shows in diagrammatic form an embodiment of an access and security scrutinizer 400 for the facility 1 according to another aspect of the present invention. The access and security scrutinizer 400 is installed at the main entrance point 12 (FIG. 1) for the facility 1. As shown in FIG. 4, the access and security scrutinizer 400 comprises a computer station 402 and a scanning antenna 404 (depicted as a broken line). The scanning antenna 404 is installed or configured around a doorway or portal 406 which leads to the interior of the healthcare facility 1. In one embodiment, the scanning antenna 404 takes the form of a RF (radio frequency) passive antenna. The RF passive antenna 404 is arranged around the perimeter of the doorway 406. The RF passive antenna 404 is compatible with RFID (radio frequency identifier) tags, which take the form of, or are incorporated as a component of, an electronic tag 410 or a temporary electronic tag 412. For example in FIG. 4, a visitor 414 (i.e. unusual non-electronic tagged personnel 306) wears a temporary electronic tag 412, and a member of medical staff 416 wears an electronic tag 410. When personal pass through the doorway 406, the identification signal emitted by the RFID tag 410 or 412 is picked up by the RF passive antenna 404, and the antenna 404 generates an output. The RF passive antenna 404 is coupled to the computer station 402. The computer station 402 executes a computer program which processes the output generated by the RF passive antenna 404 to identify the personnel wearing the electronic tag 410 or 412 based on the identification signal emitted by the RFID unit in the tag. The computer program also retrieves the record from the database associated with the personnel and a determination is made to allow the personnel further access into the facility 1. If the personnel is considered to be infected or a carrier of an infectious disease, then an alarm is initiated at the computer station 402 and the personnel is stopped from entering through the doorway 406. If the personnel is allowed access, then the database record is updated with information, e.g. the date and time the personnel entered the healthcare facility 1, and similar information is collected to track the movements of the personnel through the facility 1, e.g. the hospital, as the personnel passes by the monitoring nodes (i.e. the tracking stations 20 in FIG. 1). In this way, the movements of personnel are recorded and/or catalogued, and the event of exposure to a contagion, an exposure map or perimeter area in the healthcare facility 1 is determined and personnel having been within that area are identified as potential carriers or infected individuals. For example, an exposure zone or area may be created by defining the movements of an infected patient, visitor, or medical equipment, for example. This information is then cross-referenced with the movements of personnel in or through the area of exposure, and these personnel are identified as potential carriers.

Figure 5:
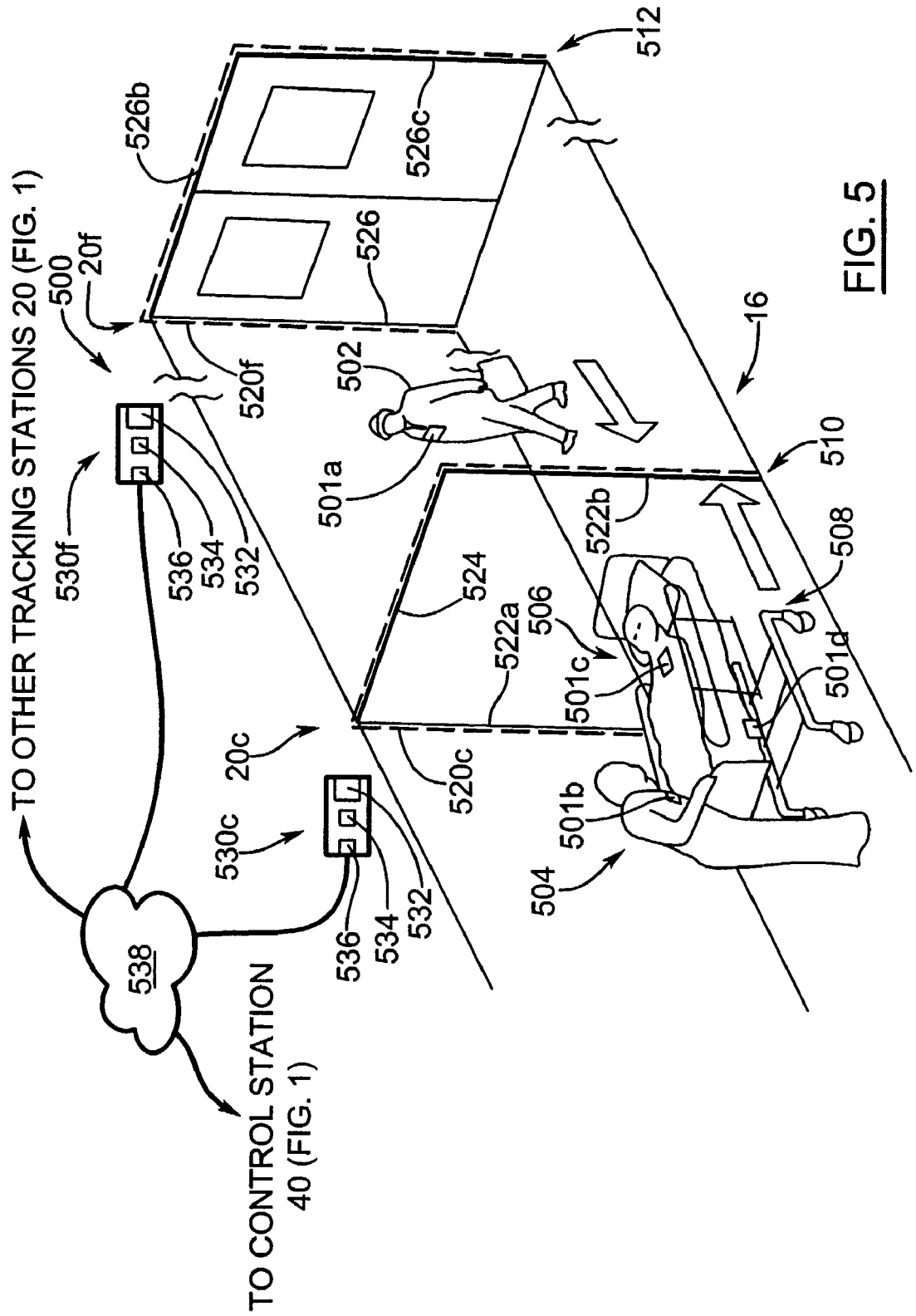
FIG. 5 shows a traffic movement tracking and scrutinizing mechanism for access points in the facility of FIGS. 2 and 3.

Reference is next made to FIG. 5, which shows in diagrammatic form a traffic movement tracking and scrutinizing arrangement or mechanism in accordance with another aspect of the present invention. The traffic movement tracking mechanism is indicated generally by reference 500 and configured for one of the corridors or hallways 16 in the healthcare facility 1 (FIG. 1). As illustrated in FIG. 5, the traffic movement tracking mechanism 500 provides the capability to track and catalogue movement through the corridor 16 by a visiting doctor 502, a resident medical staff member 504, a patient 506 and movable medical apparatus 508, with each having an electronic tag 501 attached.

As shown in FIG. 5, the traffic movement tracking and scrutinizing system 500 configured for the hallway 16 comprises a tracking station 20*c* and another tracking station 20*f*. The tracking station 20*c* is installed at a location 510 in the corridor 16. The other tracking station 20*f* is installed at a doorway 512 at one end of the hallway 16. As described above, each of the tracking stations 20*c* and 20*f* comprise a scanning antenna 520, indicated individually by references 520*c* and 520*f* in FIG. 5 (shown in broken outline). The scanning antenna 520*c* is installed around the perimeter walls 522*a* and 522*b* and the ceiling 524 at location 510 in the hallway 16. The type of scanning antenna 520*c* utilized depends on the type of transmitter devices utilized in the tags 509. According to one embodiment, RFID (Radio Frequency Identification) technology is utilized in the tags 509 and for the scanning antenna 520 as described in more detail below. For example, the scanning antenna 520*c* may be surface mounted on the walls 522 and the ceiling 524 of the corridor 16 for an existing installation, or mounted in ABS wiring tracks or conduits (not shown) below the surface for a new installation or building construction. Similarly, for the doorway 512, the scanning antenna 520*f* is mounted along the door jambs 526. Again the type and configuration of the scanning antenna 520*f* depends on the type of RFID device or transmitter utilized in the electronic tags 509.

Referring to FIG. 5, each of the tracking stations 20*c* and 20*f* also includes a communication module 530, indicated individually as 530*c* and 530*f*. The communication modules 530*c*, 530*f* correspond to the network components 22 shown in FIG. 1. The communication module 530 includes an antenna interface 532 which is coupled to the scanning antenna 520. The communication module 530 also includes a processor stage 534 and a communication interface 536. The processor stage 534 receives the signal emitted by the tag 501 and coupled by the scanning antenna 520, and processes, i.e. decodes, the received signal. The communication interface 536 couples the communication module 530 to a network 538, for example, a WAN, or the Internet as described in more detail below. Through the network 538, the communication modules 530 are coupled to a central computer or processor and database system, i.e. the control station 40 (FIG. 1). The control station 40 runs software which inputs the received signals from each of the tracking stations 20 and creates a record for each of the visiting doctor 502, the medical staff member 504, the patient 506 and the movable medical apparatus 508 in response to the detection of movement through a tracking station portal 20. The record catalogues the movement of an individual, or mobile or movable equipment throughout the facility 1. The record includes temporal data, e.g. date and time stamp, indicating the times when the person or equipment passed through each portal or was detected by the tracking stations 20. The records are stored in the database system, and made available for further processing. In one aspect, information contained in the records is used to determine an exposure zone or area, and the persons and equipment which moved through that exposure area. The exposure zone is determined by mapping the movement of individuals or equipment exposed to the virus or contagion. The exposure zone may then be used to identify other potentially infected individuals or contaminated mobile equipment based their date and time of presence within the determined zone. In another aspect, the detection of individuals or equipment by the tracking stations 20 is utilized for real-time scrutiny. For example, if mobile equipment 508 is moved without proper clearance or without being sterilized, then detection of the equipment 508 being moved triggers an alarm condition. A similar procedure is implemented for an infected patient or individual moving from their room or beyond a defined zone or area in the healthcare facility 1 (FIG. 1).

Figure 6:
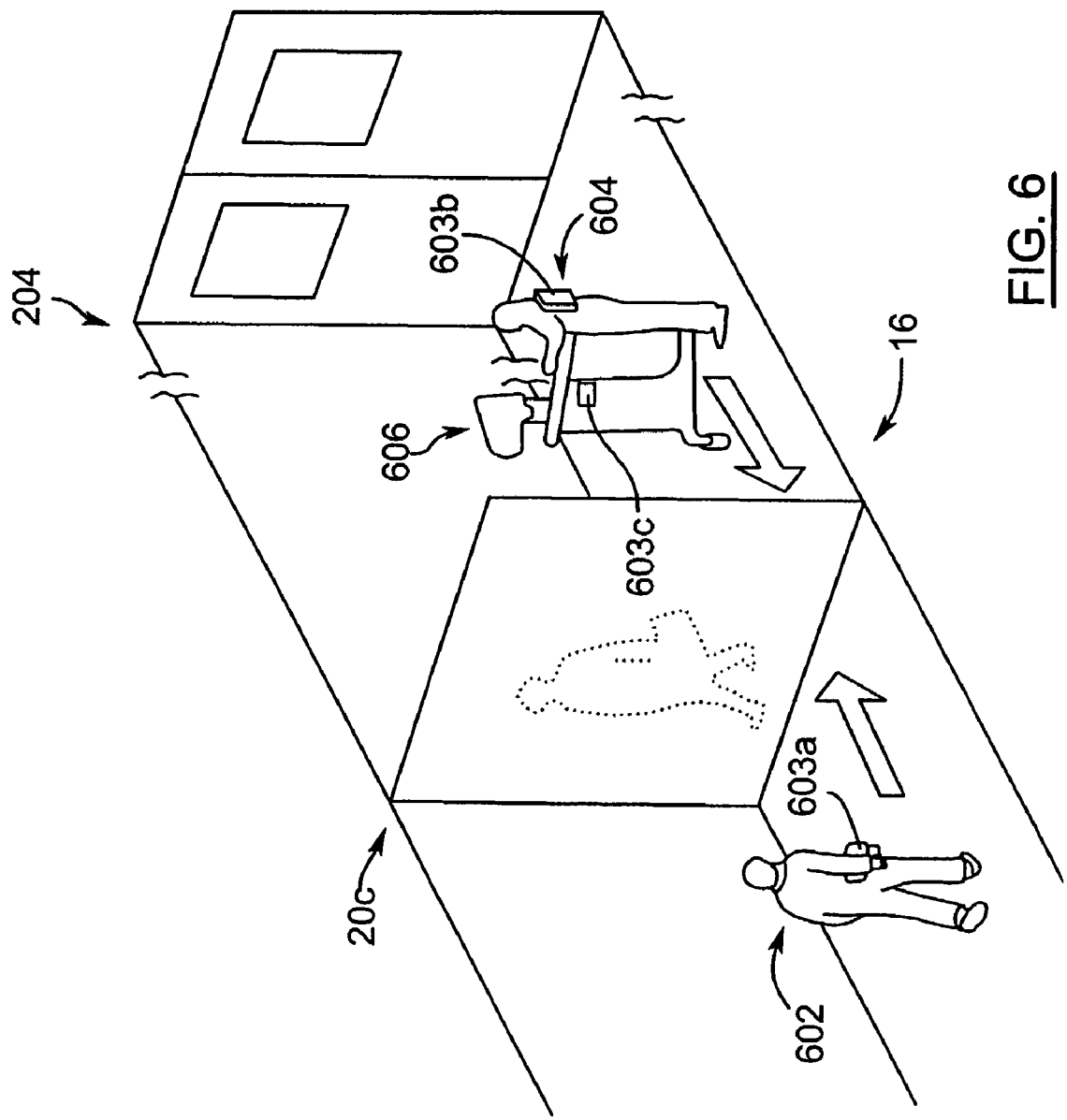
FIG. 6 shows another aspect of a traffic movement mechanism for corridors and other passage ways in the facility of FIGS. 2 and 3.

Reference is next made to FIG. 6, which shows in diagrammatic form the corridor 16 configured with tracking stations 20*c* and 20*f* as described above with reference to FIG. 5. As shown, a visitor 602 wearing an electronic tag 509 is walking down the passage way and will pass through the tracking station portal 20*c*. As shown, a hospital worker 604 is also present in the corridor 16 and is moving a mobile medical device 606 down the passageway in the direction of the tracking station 20*c*. The hospital work 604 carries an electronic tag 509, and an electronic tag 509 is also affixed to the mobile medical device 606. As the visitor 602 passes through the tracking station portal 20*c*, the scanning antenna 520*c* (FIG. 5) couples the signal emitted by the transmitter (i.e. RFID) in the tag 509, the received signal is processed and transmitted by the communication module 530*c* (FIG. 5) via the network 538 (FIG. 5) to the control station 40 (FIG. 1), a record is created or updated to catalogue the movement (i.e. time and date stamp) of the person, and the record is stored in a database, and made available for further processing. Similarly, a record is updated to catalogue the movement of the hospital worker 604 through the tracking station portal 20c. The movement of the mobile medical equipment 606 is also catalogued and the record updated as the hospital worker 604 pushes the equipment 606 through the tracking station portal 20c. The scanning antenna 520c detects the signal transmitted by the RFID in the tag 509 attached to the equipment 606, the signal received from the antenna 520c is processed by the communication module 530c and transmitted to the control station 40 (FIG. 1) via the network 538, and the record is updated and stored in the database by the control station, i.e. computer.

Figure 7:
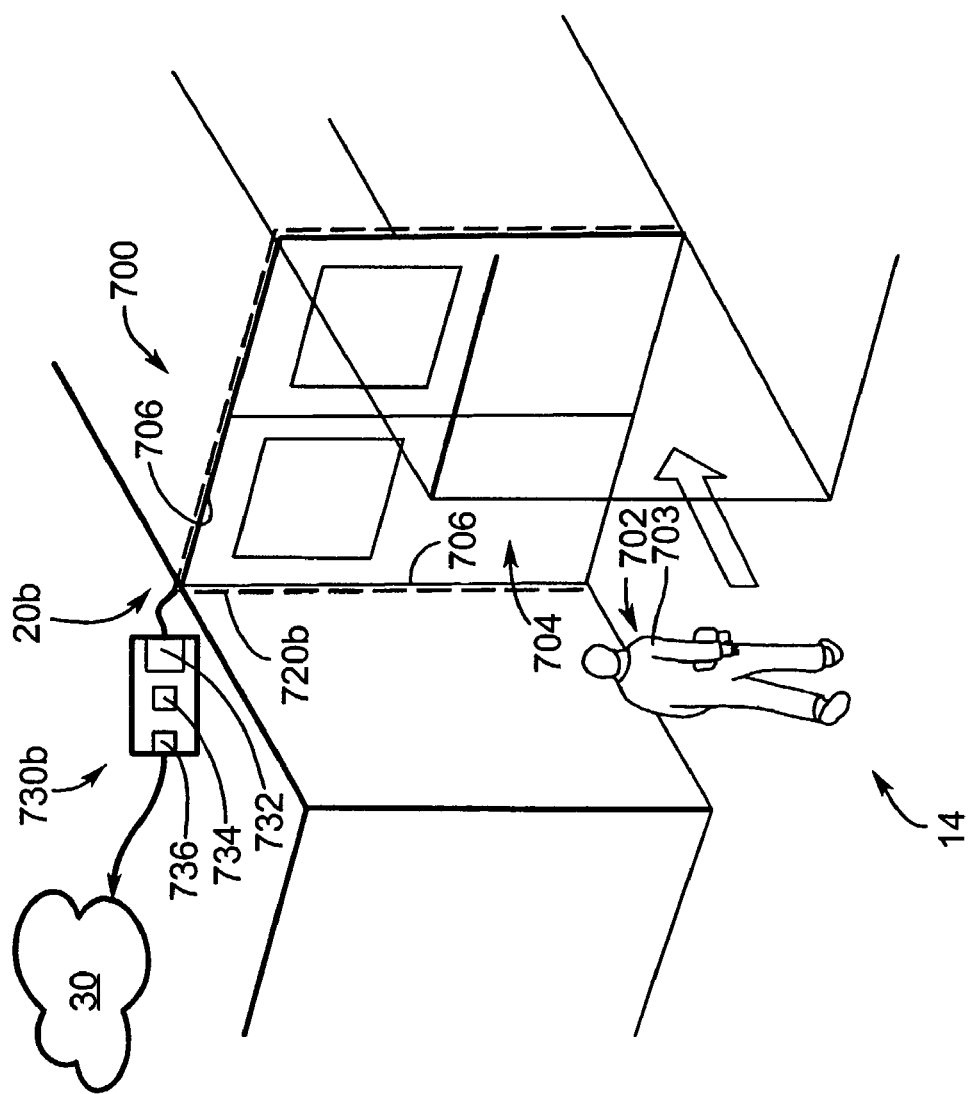
FIG. 7 shows a traffic movement mechanism suitable for tracking movement through an emergency exit in the facility of FIGS. 2 and 3.

Reference is next made to FIG. 7, which shows in diagrammatic form a tracking and cataloguing mechanism 700 for the emergency exit 14 of the healthcare facility 1 (FIG. 1) according to another aspect of the invention. The tracking mechanism 700 provides the capability to track and catalogue the movement of individuals 702 wearing an electronic tag 703, and mobile equipment which is tagged (not shown) through the emergency exit 14. There will be instances where individuals 702 will use the emergency exit 14 instead of the main entrance 12, for example, during an emergency evacuation of the healthcare facility 1 (FIG. 1), or during a security breach. In either situation, it is desirable to track and catalogue movement of the individual 702 and/or medical equipment (not shown) through the emergency exit 14.

As shown in FIG. 7, the traffic tracking mechanism 700 configured for the emergency exit 14 comprises a tracking station 20b. The tracking station 20b is installed at the doorway 704 for the emergency exit 14. As described above, the tracking station 20b comprises a scanning antenna 720b (shown as a broken line). The scanning antenna 720b is mounted along the door jambs 706 of the doorway 704. As described above, the type and configuration of the scanning antenna 720b depends on the type of RFID device or transmitter utilized in the electronic tags 509. The tracking station 20b includes a communication module 730b and corresponds to the network component 22 shown in FIG. 1. The communication module 730b includes an antenna interface 732 which is coupled to the scanning antenna 720b. The communication module 730b also includes a processor stage 734 and a communication interface 736. The processor stage 734 receives the signal emitted by the tag 703 and coupled by the scanning antenna 720b, and processes, i.e. decodes, the received signal. The communication interface 736 couples the communication module 730b to the network 30 (FIG. 1). As described above, the communication module 730b is coupled to the central computer or processor and database system, i.e. the control station 40 (FIG. 1). The control station 40 runs software which inputs the received signals from the tracking station 20b and updates the record for each individual 702 and/or tagged medical equipment (not shown) which moves through the emergency exit 14. As also described above, the record includes temporal data, e.g. date and time stamp, indicating the times when the person or equipment passed through the emergency exit portal 20b. The records are stored in the database system, and made available for further processing. In situations where there is a breach of the emergency exit 14, the records may also be used to track the movements of individuals 702.

Figure 8:
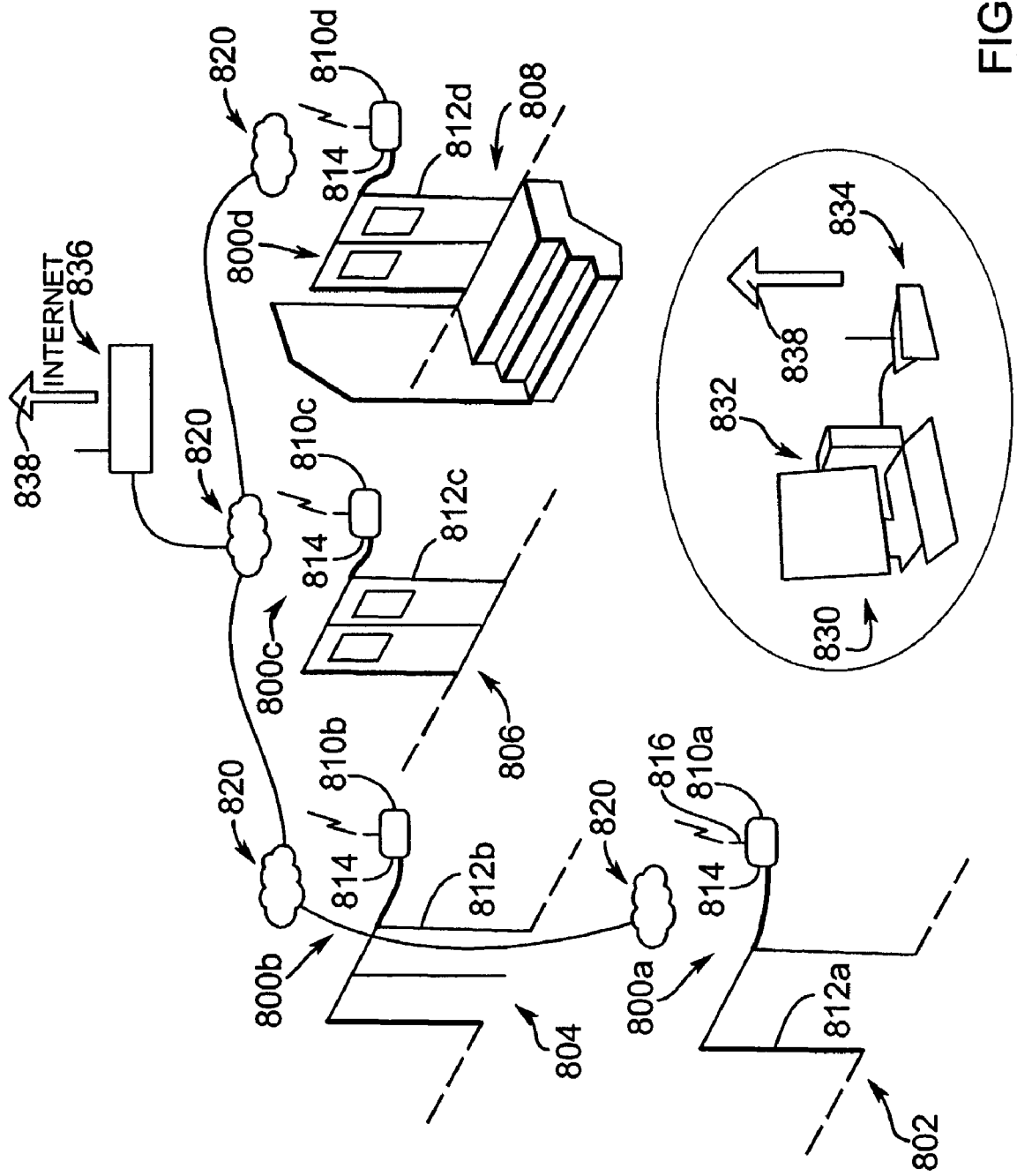
FIG. 8 shows a configuration of sub-network communication components for various entrance and exit points in a facility.

Reference is made to FIG. 8, which shows in diagrammatic form detection and communication modules 800 for various passageway, entrance and exit points in the facility 1 according to another aspect of the invention. The detection and communication modules 800 are indicated individually by references 800a, 800b, 800c, and 800d in FIG. 8. The detection and communication module 800a is configured in a corridor 802, for example, similar to the corridor 16b described above. The detection and communication module 800b is shown configured for an elevator portal 804. The detection and communication module 800c is shown configured for a door or entrance way portal 806. The detection and communication module 800d is shown configured for a stairwell or staircase portal 808. Each of the detection and communication modules 800 includes a controller module 810 and a scanning antenna 812. The controller modules 810 are shown individually by references 810a, 810b, 810c, and 810d in FIG. 8. The scanning antennae 812 are shown individually by references 812a, 812b, 812c, and 812d in FIG. 8. The controller modules 810 include an input port 814 for coupling to the scanning antenna 812. The controller modules 810 also include a communication interface 816. The scanning antenna 812 are mounted or affixed to or around the passageway opening or portal. As described above, the type of scanning antenna 812 used depends on the type of communication protocol and devices being utilized, for example, a RFID tag based system as described above, and implemented in accordance with ISO 18000-3/15693 standards.

In one embodiment, the communication interface 816 comprises a wireless implementation as illustrated in FIG. 8. For example, the communication interface 816 is implemented using the SkyGate™ series communication controller devices available from CStar Technologies Inc. of Toronto, Ontario, Canada. The communication interface 816 comprises an antenna which transmits and receives over a wireless communication channel or channels which form a wireless local area network or WLAN indicated by reference 820 in FIG. 8. The communication protocol for the WLAN 820 is defined by the communication interface 816 and the controller modules 810 used in the implementation. The WLAN 820 forms a sub-network layer which couples the detection and communication modules 800 to a central scrutinizing and management system. The central scrutinizing and management system is indicated by reference 830 in FIG. 8 and comprises a computer system 832 and a communication interface module 834. The communication interface module 834 may comprise a wireless communication module which interfaces directly with the WLAN 820. In another implementation, the communication interface module 834 includes a sub-network communication module 836. The sub-network communication module 836 provides a gateway between the sub-network WLAN 820 and the communication interface module 834. The sub-network communication module 836 communicates with the communication interface module 834 via a dedicated communication link, or via an Internet link 838. The Internet link 838 may be encrypted or otherwise secured. The Internet link 838 is suitable for multi-floor or multi-site installations. The computer system 832 may include a database server and management system and provides the functionality as described above.

Figure 9:
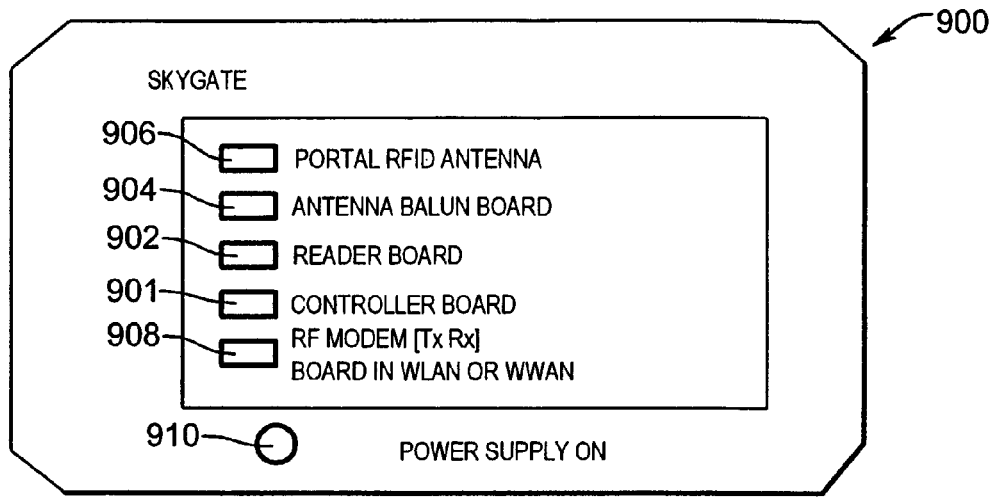
FIG. 9 shows a communication module for a wireless local area network implementation for a facility in accordance with the present invention.
Figure 10:
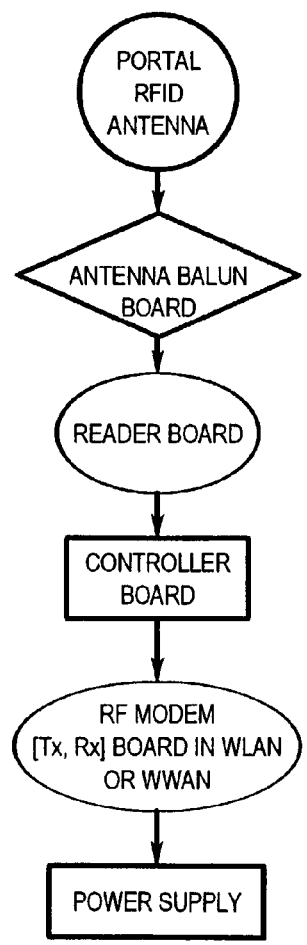
FIG. 10 shows a transmission process for the wireless local area network of FIG. 9.

Reference is next made to FIG. 9, which shows in diagrammatic form a communication controller implemented using a SkyGate™ series device from CStar Technologies Inc. The SkyGate communication controller is indicated generally by reference 900 and comprises a controller board 901, a reader board 902, an antenna Balun board 904, a RFID antenna 906, a RF modem 908, and a power supply 910. The controller board 901 includes one or more microprocessors suitably programmed to provide the required functionality. The RFID antenna 906 is tuned to receive the radio frequency signals emitted by the electronic tags (for example, the tag 509 in FIG. 5), and the received RFID signal is coupled by the antenna Balun board 904 and converted to a suitable level for the reader board 902. The reader board 902 processes the received RFID signal, for example, decoding the RFID signal, converting the RFID signal into digital format, outputting the digital signal to the controller board 901. The controller board 901 formats the digitized RFID signal into a message or packet which is then transmitted by the RF modem 908 via the WLAN (i.e. the sub-network WLAN 820 in FIG. 8). The operation of the SkyGate™ communication controller 900 is further illustrated by the flowchart shown in FIG. 10.

In one embodiment, the tracking tags are implemented using active tag technology, e.g. a TXP or Tag X-Ponder. The Tag X-Ponder comprises a PCT (Packet Coupler Transponder) which includes the power and features of a passive read/write tag operating under protocols such as supported under ISO 18000-3 standard for a proximity of vicinity activation. In addition, the TXP based tracking tag includes a UHF transmission module for sending the identifier, i.e. ID number, associated with the respective tracking tag. The TXP device is active device and includes a local power source, for example a lithium battery or cell, and operates at 3.3 volts or less, and provides a supply current in the microAmpere range. The TXP-based electronic tag remains in a "wait state or sleep mode" and is activated, i.e. "wakes up", in response to an input or trigger initiated by a RFID Interrogator terminal. The interrogator terminals are located or positioned at the tracking stations 20 in the entrance point 12, the exit 14, and the passageway corridors 16 of the facility 1 (FIG. 1) as described above. The TXP-based electronic tag includes a receiver (i.e. 13.56 MHz high frequency receiver), which is responsive to the wake-up signal and in response the TXP identifies itself using the 13.56 MHz frequency. The TXP-based electronic tag also retransmits the identifier or ID number for the electronic tag using the 433 MHz UHF communication channel which is received by the tracking station(s) 20 (FIG. 1). Using the tracking station(s) 20 and the network 30, the control module 40 under software control is then able to process and determine the location of the electronic tag, and thereby the position of the person wearing the tag. In stand-by or sleep mode, the TXP device on the electronic tag draws very little current and under normal operating conditions, the lithium power cell should provide sufficient power for about 9 years.

The interrogators or readers for the tracking stations 20 in a RFID based system are implemented using ISO 15693 Tag inlay compliant devices or technology. The ISO 15693 compatible interrogators provide for operability with RFID cards or tags, such as the TXP as described above, and RFID tags from different manufacturers, as will be within the understanding of those skilled in the art.

Figure 11:
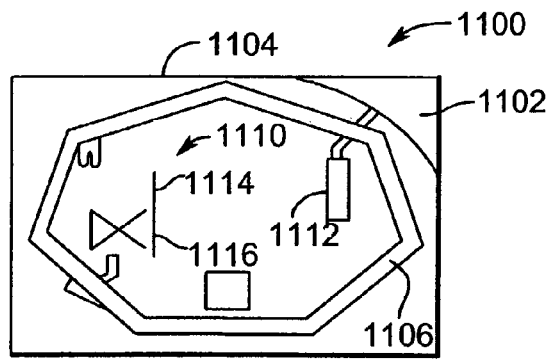
FIG. 11 shows in diagrammatic form a tag or identification card according to another aspect of the present invention.

Reference is next made to FIG. 11, which shows a RFID tag in accordance with another aspect of the invention and indicated generally by reference 1100. The RFID tag 1100 comprises a substrate or carrier 1102, a passive antenna 1104 and an active antenna 1106. The RFID tag 1100 also includes a transmitter or transceiver circuit 1110. The transceiver circuit 1110 comprises a receiver module 1112 and a transmitter module 1114. The transceiver circuitry 1110 is powered by a battery 1116. The battery 1116 also provides power for energizing and driving the active antenna 1106. The receiver module 1112 is coupled to the passive antenna 1104 and includes circuitry for receiving an interrogation signal. In response to the interrogation signal, the receiver module 1112 generates a control signal which activates the active antenna 1106 and wakes up the transmitter module 1114. The receiver module 1112 may also decouple the passive antenna 1104 in response to the interrogation signal. The transmit module 1114 may include additional circuitry for turning off the active antenna 1106 after a predetermined period or after transmission of the identification signal. It will be appreciated that the combination of the passive antenna 1104, the active antenna 1106 and the associated control circuitry provides an energy saving arrangement.

The substrate 1102 serves as the carrier for the passive antenna 1104, the active antenna 1106, the battery 1116 and electronic circuitry including the receiver module 1112 and the transmitter 1114. The substrate 1102 is fabricated to be approximately the size of a regular business card, for example, 3.25"×2.0" and approximately 0.2" thick. The tag 1100 may be fabricated using either thin film or thick film techniques. For durability, the assembled substrate 1102 is encapsulated in an impacted styrene outer casing.

The passive antenna 1104 comprises thin windings as compared to thicker windings for the active antenna 1106. Utilizing this configuration, the active antenna 1106 when not activated (i.e. energized) acts as a floating reflector for the passive antenna 1104 which is typically run at a lower frequency. Suitable frequency pairings for the passive antenna 1104 and active antenna 1106, respectively, include: 13.56 MHz passive and 466 MHz active; 13.56 MHz passive and 860 MHz active; or 860 MHz passive and 2.4 GHz active. The exact frequency range selected will be based in part on the construction techniques and building materials used in the facility 1.

Figure 12:
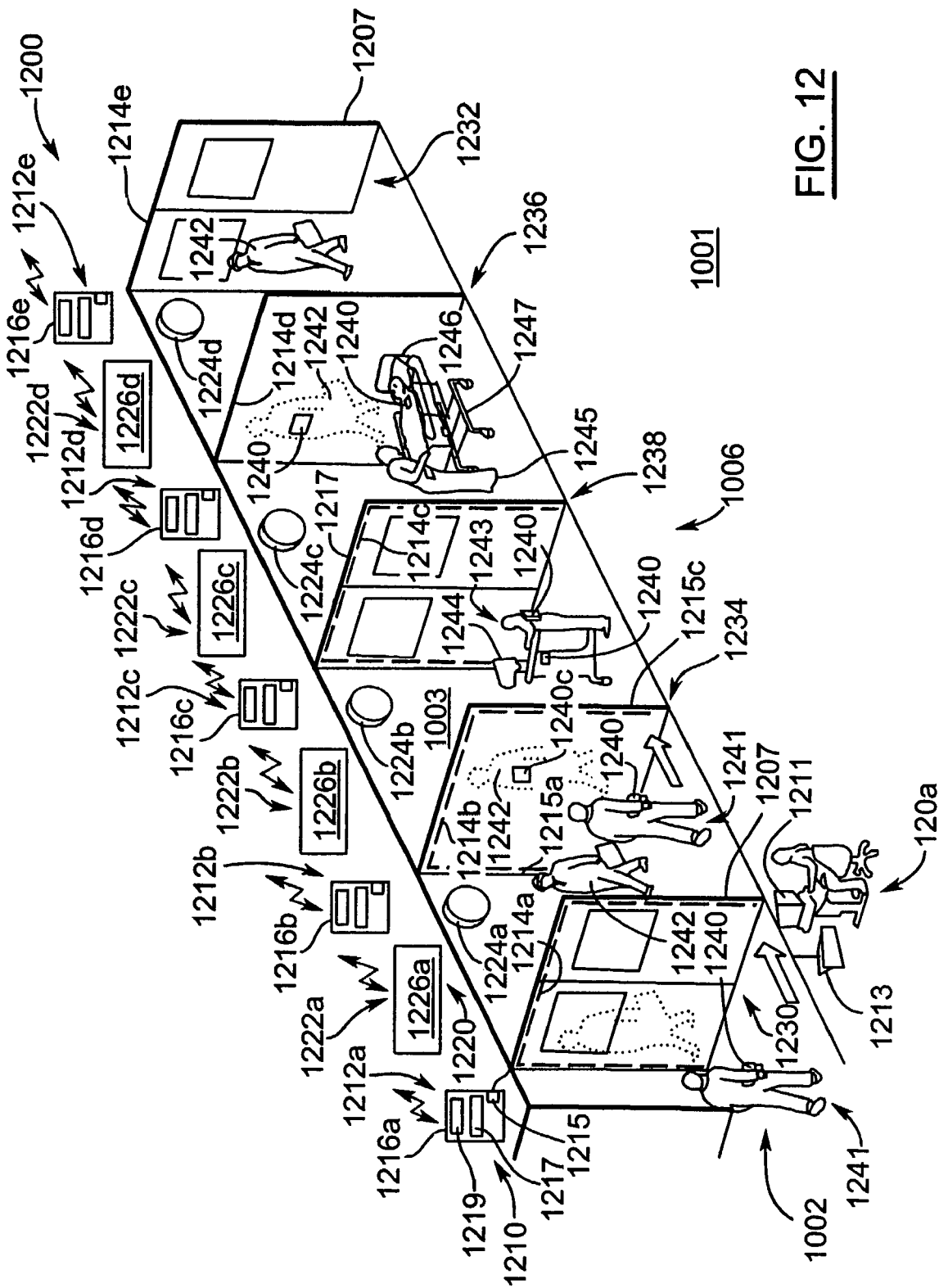
FIG. 12 shows in diagrammatic form a system for tracking and scrutinizing movement scrutinizer and a cataloguing mechanism according to another embodiment of the present invention.

Reference is next made to FIG. 12, which shows in diagrammatic form another embodiment of a system for tracking, cataloguing and delimiting movement of personnel and apparatus in a healthcare or other type of facility 1001. As depicted in FIG. 12, the facility 1001 has an entrance or front door reception area 1002 which is connected to the rest of the facility 1001 through a corridor 1006. The system is indicated generally by reference 1200. As will be described in more detail below, the system 1200 comprises a first network layer or sub-network indicated generally by reference 1210 and a second network layer or sub-network indicated generally by reference 1220. As will be described in more detail below, the first network layer or sub-network 1210 in conjunction with software performs a receiver function (which is similar to the tracking function described above). The second network layer or sub-network 1220 in conjunction with software performs a poling or supervisory function as will be described in more detail below.

The first network layer 1210 comprises a plurality of receiver stations 1212, indicated individually as 1212*a*, 1212*b*, 1212*c*, 1212*d* and 1212*e* in FIG. 12. The first receiver station 1212*a* is installed at an entrance doorway 1230 for the facility 1001. The receiver station 1212*e* is installed at another doorway 1232, for example, an exit for the facility 1001. The receiver station 1212*b* is installed in a location 1234 in the corridor or hallway 1003 for the facility 1001. Similarly, the receiver station 1212*d* is installed at another location 1236 in the hallway. The receiver station 1212*c* is installed at another doorway 1238 in the hallway. The receiver stations 1212 are similar to the tracking stations 20 described above. Each receiver station 1212 comprises an antenna 1214, shown in broken outline and individually as 1214*a*, 1214*b*, 1214*c*, 1214*d* and 1214*e* in FIG. 12. In this embodiment, the antennas 1214 are installed around perimeter walls 1215*a*, 1215*b* and 1215*c* of the hallway 1003, or in the door frame 1217 for the doorway 1230, 1232 or 1238. The antennas 1214 scan for signals (for example, a signature or other type of identification signal) and the signals are emitted by transmitters 1240. According to one embodiment, the transmitters 1240 comprise RFID tags, for example, the tag as described with reference with FIG. 11. As depicted in FIG. 12, one tag or transmitter 1240 is worn by a person 1241 (for example, a visitor) entering the facility 1001 and walking through the hallway 1003; another tag is worn by a person 1242 (for example, a physician) walking through the hallway 1003; another tag is worn by a hospital worker 1243 attending to a piece of medical equipment 1244; a tag is worn by a nurse 1245 wheeling a patient 1246 through the hallway 1003 on a gurney 1247. The patient 1246 is also assigned and wears a tag 1240. As indicated, the medical equipment 1244 includes its own tag or transmitter 1240. Similarly, the gurney 1247 has a tag 1240 attached to it.

Referring to FIG. 12, each of the receiver stations 1212 includes a communication or network interface module 1216, indicated individually as 1216*a*, 1216*b*, 1216*c*, 1216*d* and 1216*e*. The communication modules 1216 include an antenna interface or port 1215 for coupling to the respective antenna 1214. The communication module 1216 also includes a processor or controller 1217 and a network communication interface 1219. The processor 1217 receives the signal emitted by the tag 1240 and coupled by the scanning antenna 1214, and processes, i.e. decodes, the received signal. The communication interfaces 1219 and the communication modules 1216 form a communication network for the first network layer 1210, and may comprise for example, a WAN, or the Internet as described in more detail below. The first network layer 1210 is coupled to a central computer or processor and database system which runs software which inputs the received signals from each of the receiver stations 1212 (and the access and scrutinizer station 1209 described below) and creates a record for each of the physician 1242, the medical staff member 1243, the nurse 1245, the patient 1246, the movable medical equipment 1244 and the gurney 1247, in response to the detection of movement through a receiver station 1212. As described above with reference to FIG. 5, the record catalogues the movement of an individual, or mobile or movable equipment throughout the facility 1001. The record includes temporal data, e.g. date and time stamp, indicating the times when the person or equipment passed through each portal or was detected by the receiver stations 1212. The records are stored in the database system, and made available for further processing. In one aspect, information contained in the records is used to determine an exposure zone or area, and the persons and equipment which moved through that exposure area. The exposure zone is determined by mapping the movement of individuals or equipment exposed to the virus or contagion. The exposure zone may then be used to identify other potentially infected individuals or contaminated mobile equipment based their date and time of presence within the determined zone. In another aspect, the detection of individuals or equipment by the tracking stations 1212 is utilized for real-time scrutiny. For example, if mobile equipment 1244 is moved without proper clearance or without being sterilized, then detection of the equipment 1244 being moved triggers an alarm condition. A similar procedure is implemented for an infected patient or individual moving from their room or beyond a defined zone or area in the healthcare facility 1001.

As also shown in FIG. 12, the first network layer 1210 also includes an access and security scrutinizer station or module indicated generally by reference 1209. The access and security scrutinizer station 1209 is located at the entranceway to the hallway and comprises a computer station or controller 1211 and a scanning antenna or receiver module 1213. For a RFID implementation, the scanning antenna 1213 comprises a RF (radio frequency) antenna which is compatible with the RFID tags 1240 attached to medical apparatus (for example in FIG. 12, the medical equipment 1244 or the gurney 1247) or the RFID tags or badges 1240 worn by medical staff, hospital workers, visitors, patients or other personnel attending at the facility 1001 (for example in FIG. 12, the physician 1242, the visitor, the nurse 1243, and the patient 1246). When a tagged person approaches the entranceway, the identification signal emitted by the RFID tag 1240 is picked up by the RF antenna 1213 and a receive signal output is generated. The RF antenna 1213 is coupled to the computer station or controller 1211. In a manner similar to that described above with reference to FIG. 4, the computer station 1211 includes a computer program which processes the output generated by the RF passive antenna 1213 to identify the personnel wearing the electronic tag 1240 based on the identification signal emitted by the RFID unit in the tag. The computer program also retrieves the record from database associated with the personnel and a determination is made to allow the personnel further access into the facility 1001. If the personnel is considered to be infected or a carrier of an infectious disease, then an alarm is initiated at the access and security scrutinizer station 1209 and the personnel is stopped from entering through the doorway 1230. If the person is allowed access, then the database record is updated with information, e.g. the date and time the personnel entered the healthcare facility 1001, and similar information is collected to track the movements of the personnel through the facility 1001, e.g. the hospital, as the personnel passes by the receiver stations 1212 in the first network layer 1210. In this way, the movements of personnel are recorded and/or catalogued, and the event of exposure to a contagion, an exposure map or perimeter area in the healthcare facility 1001 is determined and personnel having been within that area are identified as potential carriers or infected individuals. For example, an exposure zone or area may be created by defining the movements of an infected patient, visitor, or medical equipment, for example. This information is then cross-referenced with the movements of personnel in or through the area of exposure, and these personnel are identified as potential carriers.

Figure 13:
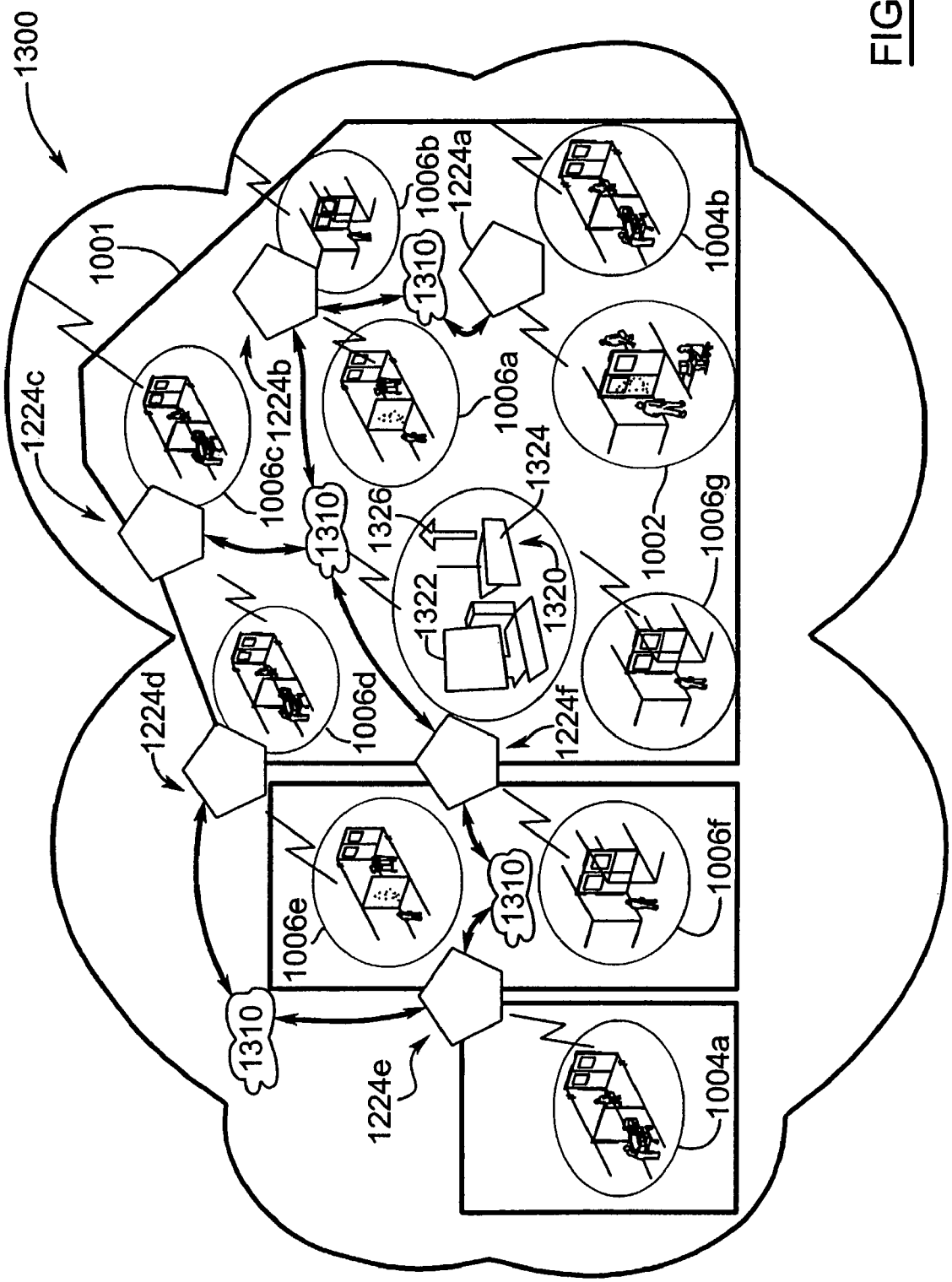
FIG. 13 shows in diagrammatic form a poling communication network for the system of FIG. 12 configured or installed in an exemplary healthcare facility.

The second network layer or sub-network 1220 provides a supervisory and regulatory function as will be described in more detail below. Referring to FIG. 12, the second network layer 1220 comprises a plurality of receiver stations or poling stations 1222, indicated individually as 1222*a*, 1222*b*, 1222*c*, and 1222*d* in FIG. 12. The poling stations 1222 are implemented using directional Balun-based receivers. The poling stations 1222 comprise an antenna 1224, e.g. a Balun antenna, and a network interface module 1226. The Balun antennas 1224 are shown individually as 1224*a*, 1224*b*, 1224*c* and 1224*d* in FIG. 12. The network interface modules 1226 are indicated individually by references 1226*a*, 1226*b*, 1226*c* and 1226*d* in FIG. 12. The network interface modules 1226 are coupled together through a communication medium 1310, for example, a wireless LAN or WAN or a wireless Internet implementation as depicted in FIG. 13. The network interface modules 1226 and the communication medium 1310 from a sub-network 1300 as will be described in more detail below with reference to FIG. 13. The poling stations 1222 are placed in locations throughout the facility 1001 and as shown for the hallway or corridor 1006, typically, in non-rf (radio frequency)-shadow locations in order to detect and pin-point operating problems or technical difficulties with the tags 1240 as they are moved through the facility 1001 either attached to personnel or apparatus. The poling stations 1222 together with the second operating layer 1220 periodically pole all the tags 1240 issued in the system. It will be appreciated that this mode of operation is in contrast to the operation of the receiver stations 1212 for the first network layer 1210. The receiver stations 1212 respond asynchronously, i.e. in response to one or more of the tags 1240 being detected in proximity of the RF passive antenna 1214 for the associated receiver station 1212.

Figure 15:
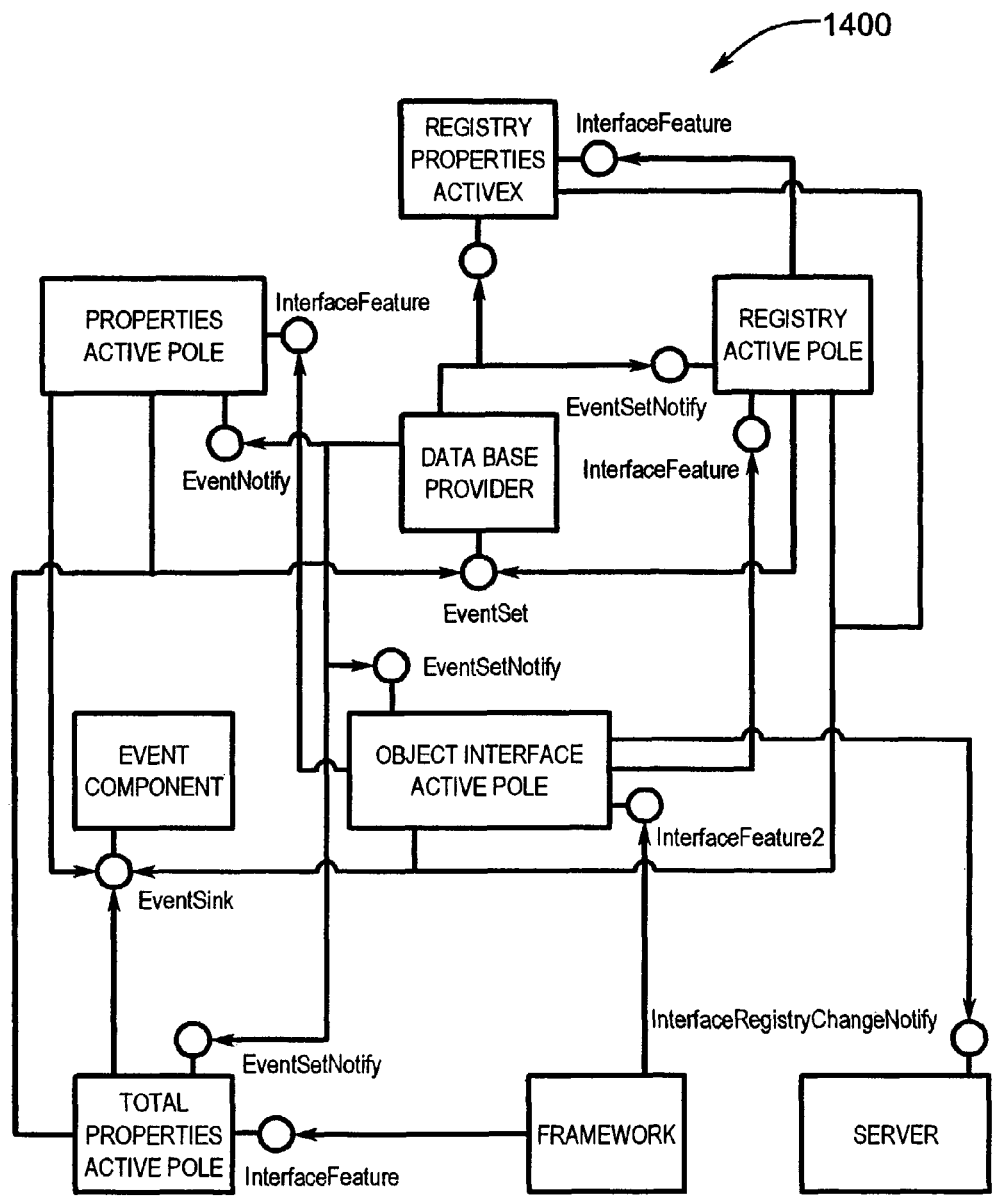
FIG. 15 shows in the form of an event flow diagram the relationship between event or receive instances and active system interrogations in accordance with this embodiment of the present invention.

In one implementation of the second network layer 1220, the poling period (i.e. interrogation frequency) may comprise 80 second intervals. An exemplary implementation for a software architecture (indicated by reference 1500) is shown in FIG. 15. As will be described in more detail below the operating software 1500 comprises a monitoring and cataloguing module 1510 for the first network layer and a supervision and regulation module 1540 for the second network layer 1520. According to this aspect, the supervision and regulation module 1540 includes a functional module or routine 1554 for reconciling tags 1240, i.e. "off-duty" personnel which have left the facility 1001 and are indicated as missing by the system in response to the poling operations. This function 1554 takes into account that personnel and staff (e.g. doctors and nurses, contractors and other temporary visitors) will come and go on certain shifts or during certain time periods, and their associated tags 1240 will not be detectable by the system.

Reference is next made to FIG. 13, which shows in diagrammatic form the sub-network 1300 formed from the poling stations 1222 coupled to the communication medium 1310. In FIGS. 12 and 13, like references indicate like components or elements. The poling stations 1222 are coupled to each other through the communication medium 1310 and also to a computer or control station indicated by reference 1320. The control station 1320 comprises a computer 1322 and a communication module 1324. The computer 1322 is suitably programmed, i.e. executes a computer program, to provide the functionality associated with the second network layer 1220, for example, decoding, processing and recording the received poling signals, as described above. The communication medium 1310 may comprise a wired or wireless implementation for a local area network (LAN), a wide area network (WAN) or a virtual private network (VPN) configured using the Internet. For a wireless implementation, SkyGate™ series communication controller devices available from CStar Technologies Inc. of Toronto, Ontario, Canada, may be used in a similar manner as described above with reference to FIG. 8. It will be appreciated that a wireless implementation provides greater flexibility for reconfiguring the sub-network 1300 for one or more floors in the facility 1001, and/or connecting the sub-network. 1300 to corresponding sub-networks on other floors in the facility 1001. The communication module 1324 may comprise a wireless communication module which interfaces with the communication medium, i.e. network, 1310. The communication module 1324 may also include an Internet enabled communication interface 1326 and provides a communication interface for transmitting data and other information to a central computer in the facility 1001 or located at some other remote site or other facility.

Figure 14:
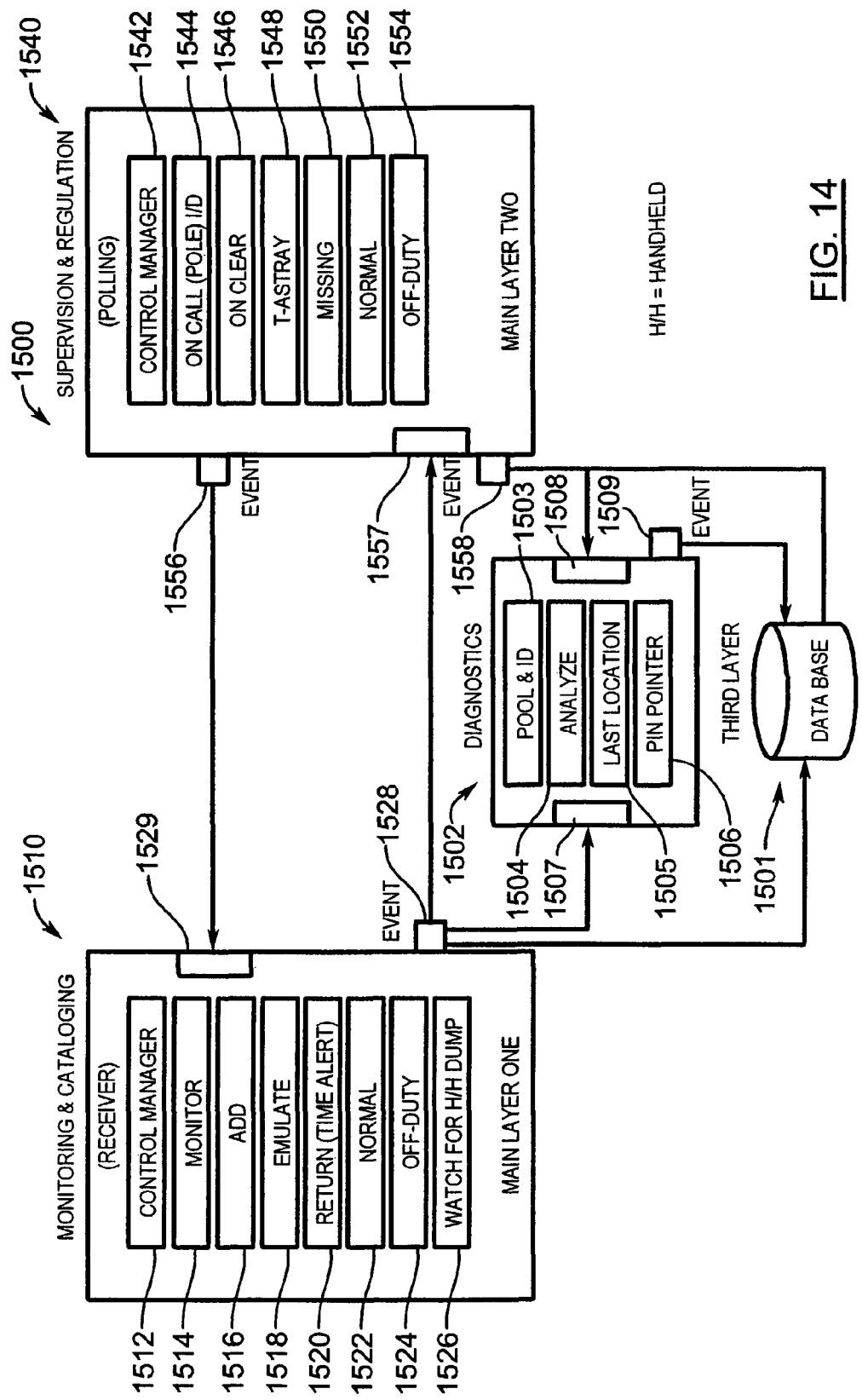
FIG. 14 shows in diagrammatic form a control system or architecture for the system and database of FIG. 12.

Reference is next made to FIG. 14, which shows in block diagram form a computer program or software architecture for the system according to the second embodiment of the invention. The system software is indicated generally by reference 1500 and comprises the monitoring and cataloguing module 1510 and the supervision and regulation module 1540 as introduced above. In addition, the system software 1500 includes a database module 1501 and a diagnostics module 1502 according to another aspect of the invention.

The monitoring and cataloguing module 1510 provides control and functionality for the first network layer or sub-network 1210 and may be implemented in a manner similar to that described above with reference to FIGS. 2 and 3. The monitoring and cataloguing module 1510 interfaces with both the database server 1501 and the diagnostics module 1502. The database server 1501 is used to store tracking and event information as described above. As shown in FIG. 14, the monitoring and cataloguing module 1510 comprises a number of functional or program modules including a control manager 1512, a monitor 1514, an event add module 1516, an emulation module 1518, a return or time alert module 1520, a normal operation module 1522, an off-duty module 1524, and a handheld interface module 1526. As shown in FIG. 14, the monitoring and cataloguing module 1510 includes an output port or interface 1528 for transferring information and data with the supervision and regulation module 1540, the database server 1501 and the diagnostics module 1502. The monitoring and cataloguing module 1510 includes an input port 1529 for receiving information and data from the supervision and regulation module 1540.

The control manager 1512 comprises a kernel or operating system component for the monitoring and cataloguing module 1510, which oversees or controls the resources associated with the software module and/or functional components. The control manager 1512 is implemented in software as will be readily understood by one skilled in the art.

The monitor 1514 comprises a program or software module for monitoring the detection and movement of tags associated with personnel, visitors, medical equipment and/or apparatus as they move or travel through the facility 1001, for example, as described above. The monitor 1514 is coded in software as will be readily understood by one skilled in the art.

The event add module 1516 comprises a program or software module which functions to store or add an event associated with the activity of a tagged person or apparatus to the database module 1501. The event add module 1516 is implemented or coded as will be readily understood by one skilled in the art.

The emulation or comparison module 1518 comprises a program or software module which functions to compare registered or catalogued events (data) against poled events or data. The emulation module 1518 is implemented or coded as will be readily understood by one skilled in the art.

The return or time alert module 1520 comprises a program or software module which functions to set or transmit an alarm in response to an exception condition, e.g. a missing tag or a non-functioning tag. The alarm may be transmitted as a signal to a security facility or department which then takes additional measures. The return or time alert module 1520 is implemented or coded as will be readily understood by one skilled in the art.

The normal operation module 1522 comprises a program or software module which provides the functionality associated with healthful or normal times in the facility as described above with reference to FIG. 2. The normal operation module 1522 is implemented or coded as will be readily understood by one skilled in the art.

The off-duty module 1524 comprises a program or software module which provides tracking functions associated with personnel who have left the facility or are 'off-duty', for example, a human or person who is not an outside construction contractor or a patient, but rather a worker (e.g. a nurse or a doctor) who is off-duty, but may be called back to the facility as required. The off-duty module 1524 is implemented or coded as will be readily understood by one skilled in the art.

The handheld interface module 1526 comprises a program or software module which provides an interface for communicating with and storing data received from a handheld device from a physician as described in more detail below with reference to FIG. 17. The handheld interface module 1526 is implemented or coded as will be readily understood by one skilled in the art.

The supervision and regulation module 1540 comprises a control manager module 1542, an on-call input/output module 1544, an on-clear module 1546, a tag-astray module 1548, a tag missing module 1550, a normal state module 1552, and off-duty state module 1554. As shown, the supervision and regulation module 1540 includes interfaces 1556, 1558 for exchanging poling related information and other data with the monitoring and cataloguing module 1510 and the database server 1501 and the diagnostics module 1502, respectively. The supervision and regulation module 1540 also includes an input port 1557 for receiving information and data from the monitoring and cataloguing module 1510.

The control manager 1542 comprises a kernel or operating system component for controlling operation of the supervision and regulation module 1540. The control manager 1542 is implemented in software as will be readily understood by one skilled in the art.

The on-call input/output module 1544 comprises a program or software module for monitoring and handling personnel (e.g. hospital staff such as nurses or doctors) who may be called back as needed. The on-call input/output module 1544 is coded in software as will be readily understood by one skilled in the art.

The on-clear module 1546 comprises a program or software module for handling the condition or state where the system is functioning without any exception, emergency or other abnormal event or occurrence in the facility and/or system. The on-clear module 1546 is coded in software as will be readily understood by one skilled in the art.

The tag-astray module 1548 comprises a program or software module for determining and recording/cataloguing tags (personnel or equipment) which have gone astray or missing, for example, as described above. The tag-astray module 1548 is coded in software as will be readily understood by one skilled in the art.

The missing tag module 1550 comprises a program or software module for determining whether a tag is missing from the facility 1001. If it is determined that a tag is missing, i.e. no response is received within a predetermined period to the poling request and the tag does not correspond to an off-duty worker (i.e. utilizing the Off-Duty module 1554), then the last known location of the missing tag is determined from the corresponding data stored for that tag in the database server 1502. For example, the pin point module 1506 may be invoked in the diagnostics module 1502 to 'pin-point' the last known location of the missing tag. The missing tag module 1550 is coded in software as will be readily understood by one skilled in the art.

The normal module 1552 comprises a program or software module for determining and ascertaining whether the poled tags are operating normally, for example, as described above. The normal module 1552 is coded in software as will be readily understood by one skilled in the art.

The off-duty module 1554 comprises a program or software module for monitoring and handling personnel (e.g. hospital staff such as nurses or doctors) who are off-duty (and may be called back as needed). The off-duty module 1554 is coded in software as will be readily understood by one skilled in the art.

The diagnostics module 1502 comprises a program or software module which runs between the monitoring and cataloguing module 1510 and the supervision and regulation module 1540, i.e. the first network layer or sub-network 1510 and the second network layer or sub-network 1520. The diagnostics module 1502 comprises a number of functional or program modules including a tag pool and identification module 1503, an analysis module 1504, a tag last location module 1505, and tag pin pointer or locator module 1506. The diagnostics module 1502 also includes an input port 1507 for receiving data from the monitoring and cataloguing module 1510 and another input port 1508 for receiving data from the supervision and regulation module 1540. The diagnostics module 1502 further includes an output port or interface 1509 for exchanging information or data with the database server 1501. The diagnostics module 1502 may comprise a registry model as shown in FIG. 15.

The pool and I/D (identification) module 1503 comprises a program module or function for pooling (i.e. grouping) humans or assets and identifying humans or assets in the pools or groups. For example, doctors and nurses may be grouped in a staff pool, patients grouped in a patient pool, and assets (e.g. x-ray machines, ultrasound machines) grouped in a medical equipment pool. The pool and I/D module 1503 is implemented in software as will be readily understood by one skilled in the art.

The analyze module 1504 comprises a program module or function for analyzing data associated with a tag or tag event. The data is received from either the monitoring and cataloguing module 1510 and/or the supervision and regulation module 1540. The analyze module 1504 is implemented in software as will be readily understood by one skilled in the art.

The last location module 1505 comprises a program module or function which determines a last location indication for a tag of interest using information or data received from the monitoring and cataloguing module 1510 and/or the supervision and regulation module 1540. The last location module 1505 is implemented in software as will be readily understood by one skilled in the art.

The pin pointer module 1506 comprises a program module or function for 'pin-pointing' the last known location of a tag which has been determined to be missing (i.e. utilizing the missing module 1550). This information is then relayed to the last location module 1505 which transmits the data for storage in the database server 1501. The pin pointer module 1506 is implemented in software as will be readily understood by one skilled in the art.

The database server 1501 stores information or data received from the monitoring and cataloguing module 1510, the supervision and regulation module 1540, and from the diagnostics module 1502. Data from the monitoring and cataloguing module 1510 includes information about the movement of personnel which is tracked using monitoring nodes located throughout the facility 1001, for example, 1212*a*, 1212*b*, 1212*c*, 1212*d* and 1212*e* as illustrated in FIG. 12. The database server 1501 may be implemented in a similar manner to the database 229 described above with reference to FIGS. 2 and 3, with the addition of data inputs from the diagnostics module 1502 and the supervision and regulation module 1540.

Reference is next made to FIG. 15, which shows in the form of an event flow diagram a registry model for the diagnostics module 1502 and is indicated generally by reference 1400. The registry model 1400 functions to establish a relationship (i.e. occurrence incidence and correlation) between a tag (i.e. instance of the object) when monitored by the first network layer 1210 (FIG. 12) and the tag (i.e. an active object) when poled by the second network layer 1220 (FIG. 12).

Figure 16:
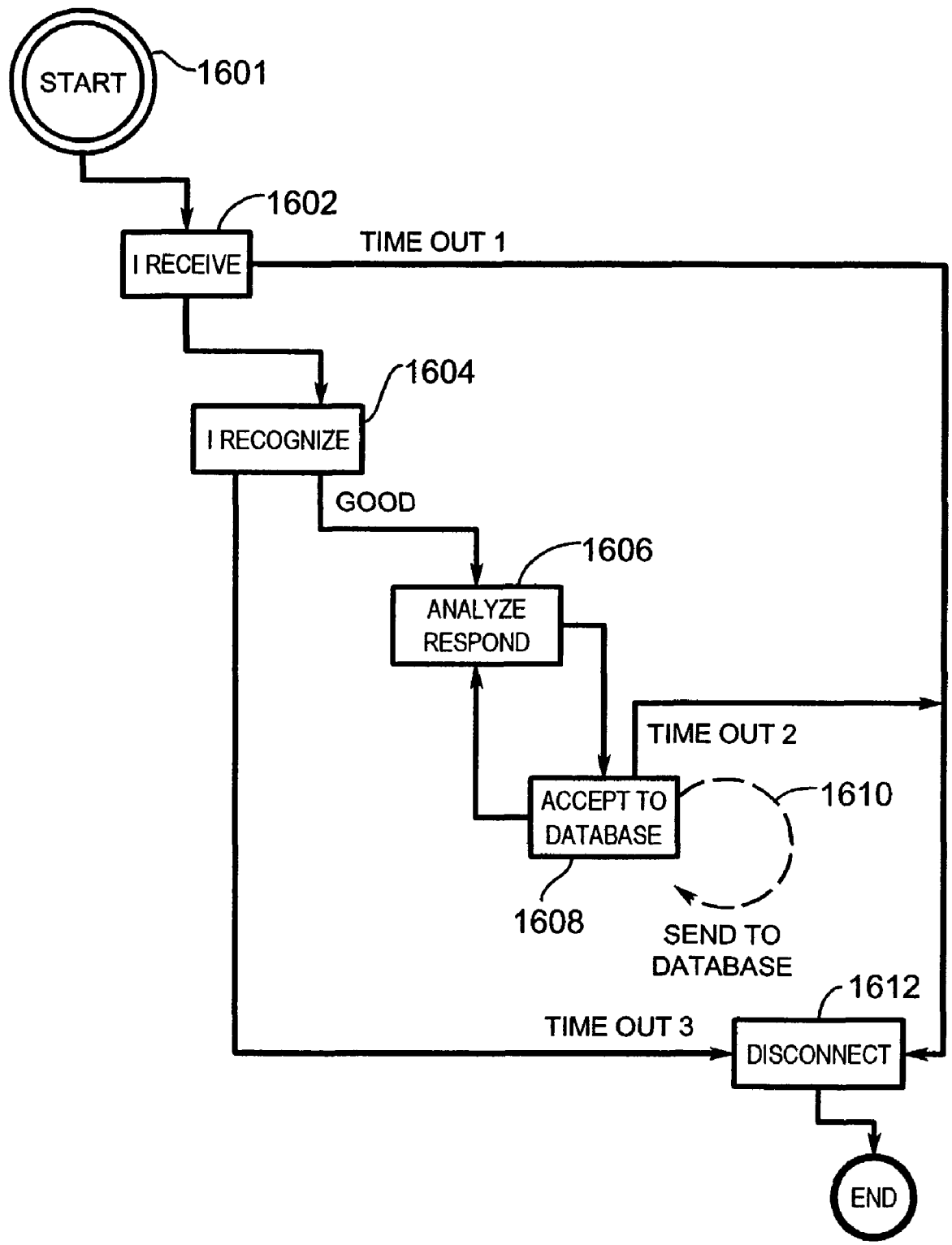
FIG. 16 shows in state diagram form a diagnostics procedure for each of the poling antennas or nodes.

Reference is next made to FIG. 16, which shows in state diagram form the function at the poling stations 1222 operating under the second network layer 1220 (i.e. directional Balun-based receivers as described above with reference to FIG. 12). The poling station transmits (1601) a poling request or command and waits for a response (1602). If a response is not received from all of tags before a predetermined period of time, a time out will occur. This time out, i.e. time out 1, is recorded by the supervision and regulation module 1540 (FIG. 14) against the tag(s) which did not respond in time, and further processing is performed to determine whether the unresponsive tag(s) has malfunctioned or left the facility with or without authorization. The responses which are received by the poling stations 1222 are processed for recognition in the system (1604). The responses of the tags which are recognized (in 1604) are then analyzed (1606). Responses from tags which are not recognized (in 1604) are marked with a time out (Time Out 3). The responses are analyzed (in 1606) and presented for acceptance (in 1608) for storage in the database. For example, construction contractors who enter and leave the facility on multiple and random times during the course of day (e.g. to retrieve tools, building supplies, take lunch or coffee breaks) will have an acceptance criteria which takes into account the random nature of their movements. The response data may be sent back for additional analysis for acceptance at 1608. Once accepted, the data for each of the accepted tag responses is transmitted to the database for storage. If any of the data is deemed not acceptable, then a time out (Time Out 2) is written against the relative tag(s). The completion of the poling sequence comprises a disconnect operation 1612.

Figure 17:
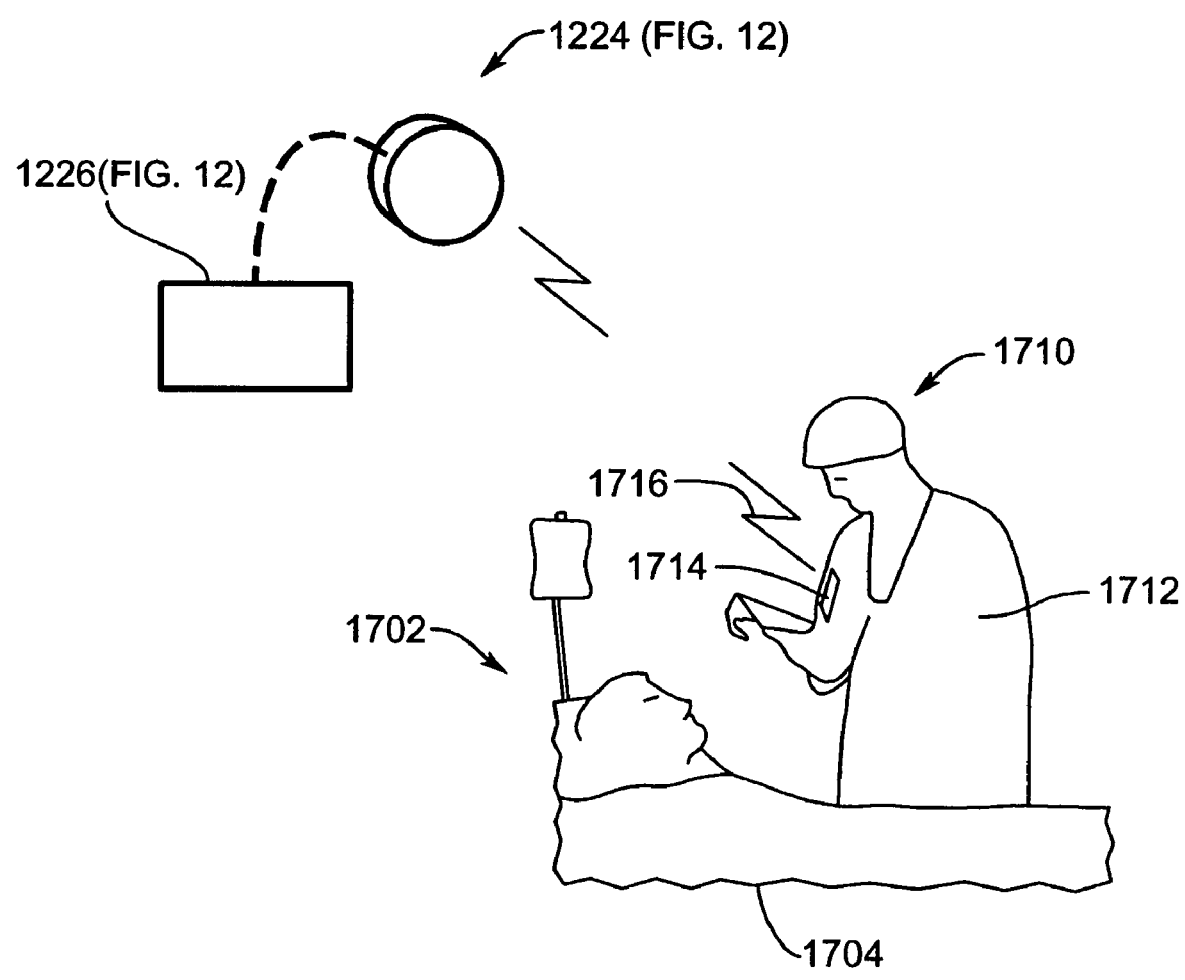
FIG. 17 shows in diagrammatic form another function for a poling station in the context of a physician and a patient in a healthcare facility.

Reference is next made to FIG. 17, which shows in diagrammatic form a poling clinical feed-back loop indicated generally by reference 1700. The poling clinical feed-back loop 1700 provides a containment mechanism or facility, for example, in the case of a major or fast moving epidemic for a patient 1702 without completing the complete admission procedure as described above. According to this aspect of the invention, the patient is assigned a RFID tag 1704 and then emergency medical measures and treatments may be provided without the need for knowing the name of the patient 1702. A physician 1710 attends to the patient 1702, and the physician 1710 is assigned a RFID tag 1712 in accordance with the procedure as described above. As shown in FIG. 17, the physician 1710 utilizes a handheld digital device 1714, for example, a personal digital assistant or PDA, having a wireless communication link 1716, for example, a read/write RFID modem. The wireless communication link 1716 interfaces with the Balun antenna 1224 for the poling station 1222 (as described above with reference FIG. 12). In operation, the poling clinical feed-back loop 1700 allows the patient 1702 (once assigned the RFID tag 1704) to be admitted to "Triage" or the "The Bull Pen", i.e. the emergency room facility where patients are first examined or treated by a doctor in a hospital. The doctor 1710 (or attending paramedic as described below) reads the RFID tag 1704 on the wrist of the patient 1702 to obtain the patient's identification number and the current clinical status for the patient 1702. While the doctor 1710 talks to or examines the patient 1702, a 'poling cycle' (e.g. 80 second pole) occurs and the second network layer 1220 (FIG. 12) recognizes the identification number for the patient 1702, the identification number for the doctor 1710 and the identification number associated or assigned to the handheld device 1714. The system utilizes the second network layer 1220 to update the handheld device 1714 with clinical status of the patient and amendments to the patient status are compared (for example, automatically in the handheld device 1714). In accordance with this aspect, the system may include a software function or component for updating the clinical status of the patient 1702 based on prior knowledge of the patient's identification number and before the doctor's visit to the location of the patient 1702. The software component utilizes the second network layer 1220 to 'pole' the handheld device 1714 and download the clinical status of the patient in response to the patient identification number selected or displayed on the handheld device 1714 by the doctor 1710. If during examination of the patient 1702, the doctor 1710 adds new data or changes the data, for example, the doctor 1710 adds a new prescription, then the system tracks the change with a new amendment number for the database record associated with the patient 1702 through the clinical feed-back loop applied at the next poling interval (e.g. 80-second pole). The updated data may also remain on the handheld device 1714 together with the previous data for the patient 1702 if so required by the doctor 1710, or for transfers to other databases if so required.

In accordance with this aspect, the database 1501 (FIG. 14) may includes a "Dispatch" layer for recording the data associated with treatment of the patient 1702 in "Triage" or "Moulage" or the data received from the physician 1710 using the handheld device 1714. The Dispatch layer can be associated with an overall "Incident Management System" architecture as described in more detail below with reference to FIG. 18.

The clinical feed-back loop 1700 mechanism is also suitable for patients in "Moulage", i.e. where paramedic crews are held with less seriously injured or less critically ill patients. The paramedics may be provided with one or more of the handheld devices 1714 to record treatment or diagnosis data. In "Moulage", paramedics attend to the lesser injured patients. After the tumult and mayhem of the original disaster has settled down, the emergency room doctors 1710 become available to attend to the patients originally admitted to "Moulage".

Figure 18:
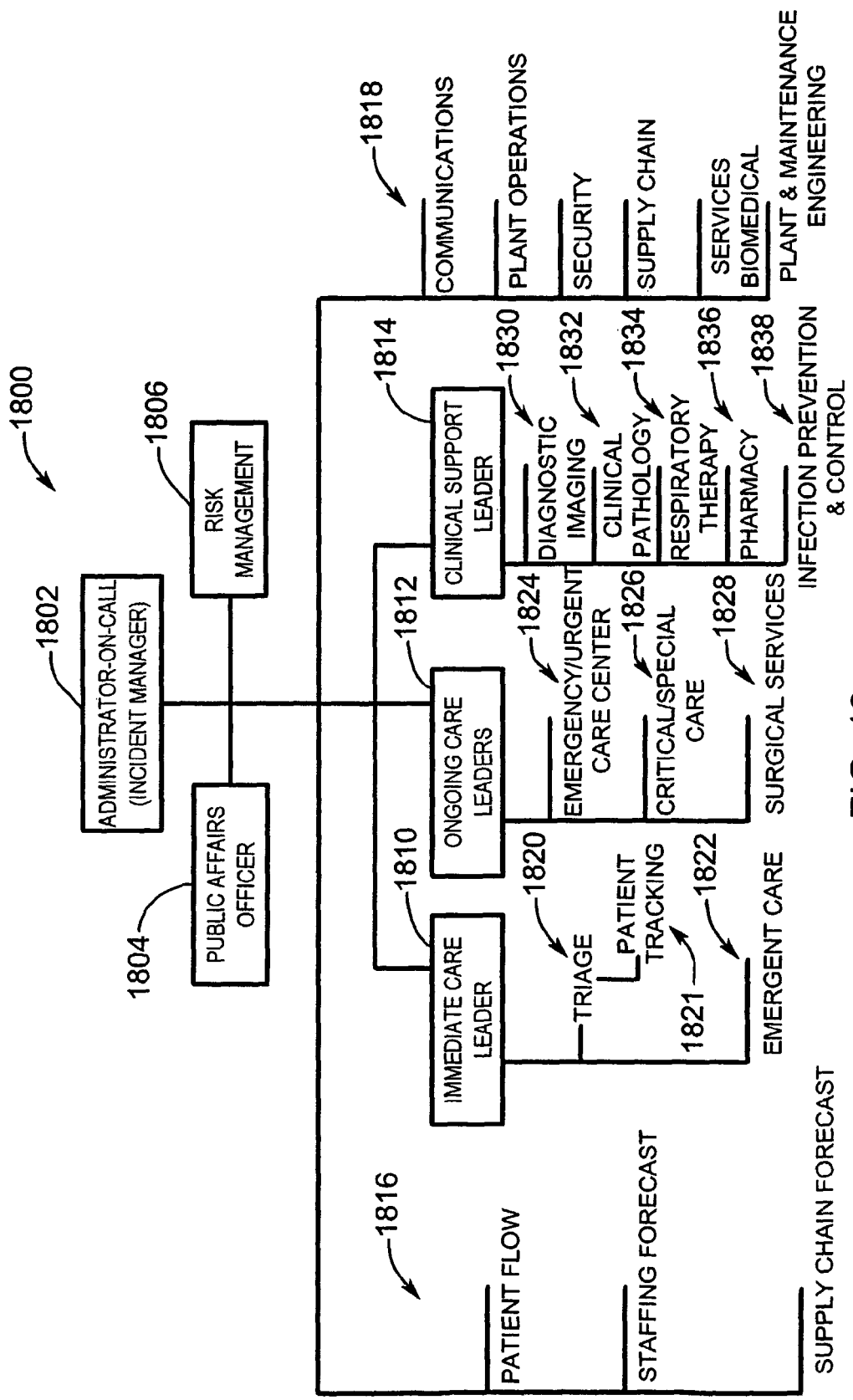
FIG. 18 shows in schematic form an incident and event management mechanism according to another aspect of the present invention.

Reference is next made to FIG. 18 which shows in schematic form an Incident and Event Management architecture or system suitable for use with the system and methods according to the present invention. The Incident and Event Management system is indicated generally by reference 1800. As depicted in FIG. 18, the Incident and Event Management 1800 includes an incident manager 1802, a public affairs officer 1804 and a risk management position 1806 at the top level or tier. The incident manager 18b2 oversees or manages an immediate care leader 1810, an ongoing care leader 1812, and a clinical support leader 1814. The incident or administrative manager 1802 also manages functions 1816 associated with patient flow, staffing forecasts, and supply chain forecasts, and functions 1818 associated with communications, plant operations, security, supply chain, biomedical services and plant & maintenance engineering.

As depicted in FIG. 18, the immediate care leader 1810 oversees triage 1820 and emergent care 1822. The ongoing care leader 1812 oversees the emergency/urgent care center 1824, critical/special care 1826 and surgical services 1828. The clinical support leader 1814 oversees diagnostic imaging 1830, clinical pathology 1832, respiratory therapy 1834, pharmacy 1836, and infection prevention and control 1838. According to this aspect, the poling or supervisory network 1220 (FIG. 12) functions in conjunction with the Incident and Event Management in the hospital to gather and record data. For example, as discussed above with reference to FIG. 17, disaster management data or clinical data is gathered for the patient 1702 (FIG. 17) admitted to triage 1820. The first network layer 1210 (FIG. 12) also provides for patient tracking 1821. The second network layer 1220 (FIG. 12) also provides a poling or supervisory function for tracking the patient. In accordance with this aspect, the first network layer 1210 (FIG. 12) and/or the second network layer 1220 (FIG. 12) provides a real-time and on-line mechanism for managing patient flow 1816, emergent care 1822, the emergency/urgent care center 1824, the critical/special care unit 1826, the surgical services unit 1828, diagnostic imaging 1830 and infection prevention and control 1838.

Figure 19:
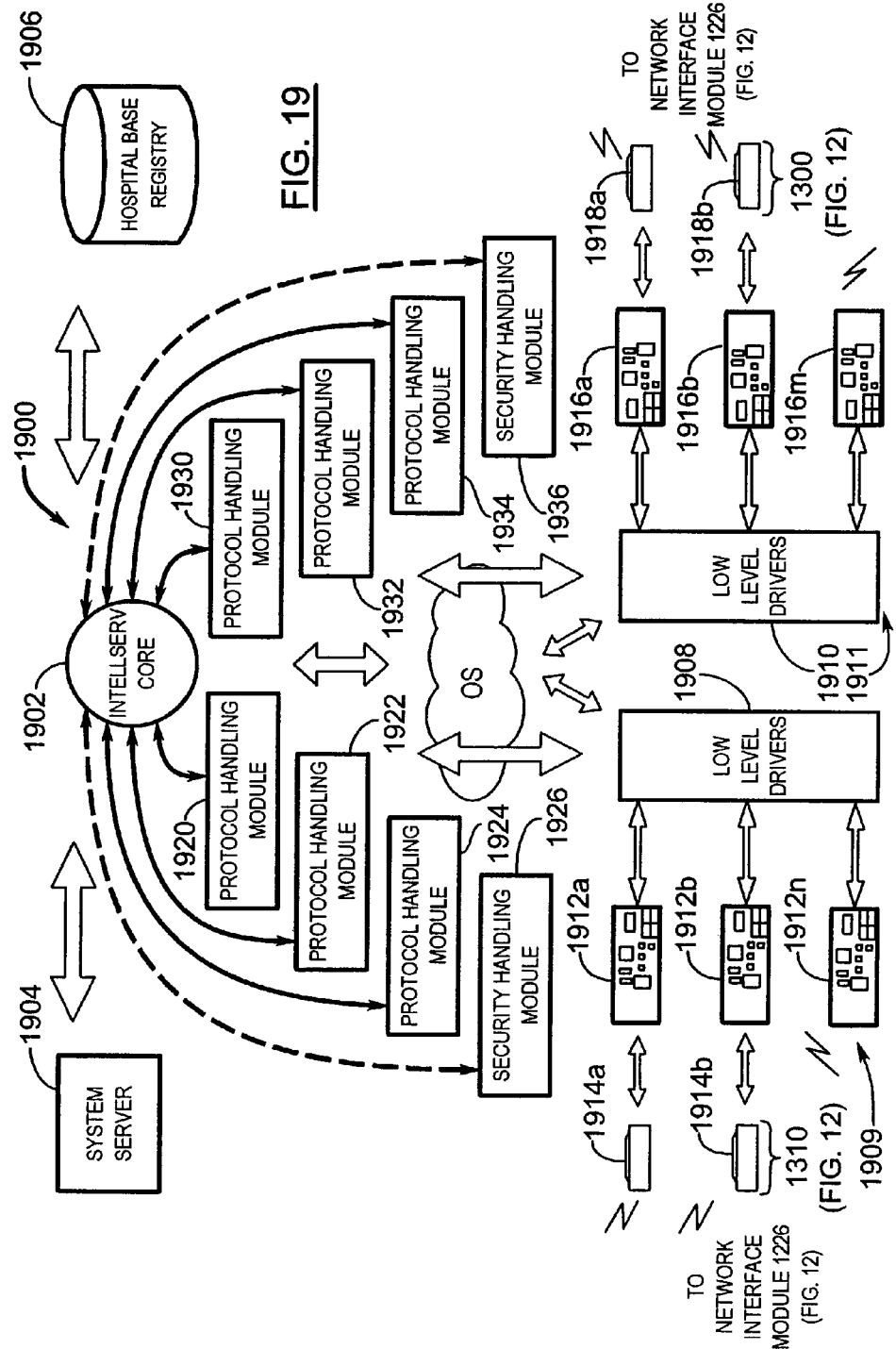
FIG. 19 shows in schematic form a poling based operating system for auditing movement of personnel within a healthcare facility according to another aspect of the present invention.

Reference is next made to FIG. 19, which shows in diagrammatic an implementation for an operating system architecture for the second network layer or poling sub-network 1220 (FIG. 12). The operating system architecture is indicated generally by reference 1900 and comprises a server kernel or server processor 1902. The server kernel 1902 interfaces to the system server 1904 and to the hospital base registry 1906. The server kernel 1902 also interfaces to low level drivers 1908 for a central uplink facility 1909 and to low level drivers for a hospital security downlink facility 1911. As shown in FIG. 19, the low level drivers 1908 provide an interface to the network and communication hardware comprising interface boards 1912, shown individually as 1912a, 1912b, ... 1912n, and modems 1914, shown individually as 1914a, 1914b... in FIG. 19. Similarly, the low level drivers 1910 for the hospital security downlink provide an interface to the network and communication hardware comprising interface boards 1916, shown individually as 1916a, 1916b, ... 1916m, and modems 1918, shown individually as 1918a, 1918b... in FIG. 19. The modems 1914 (1916) are coupled to the network interface modules 1226 (FIG. 12) via the wireless communication network 1310 (FIG. 13).

For the central uplink facility 1909, the server kernel 1902 includes protocol handling modules 1920, 1922, 1924 and a security handling module 1926. Similarly, for hospital security downlink 1911, the server kernel 1902 includes protocol handling modules 1930, 1932, 1934 and a security handling module 1936.

In operation, the server kernel 1902 utilizes one or more of the protocol handling modules 1920, 1922 or 1924 to 'pole' or 'ping' the RFID tags present in the facility 1001 (FIG. 12).

Figure 20:
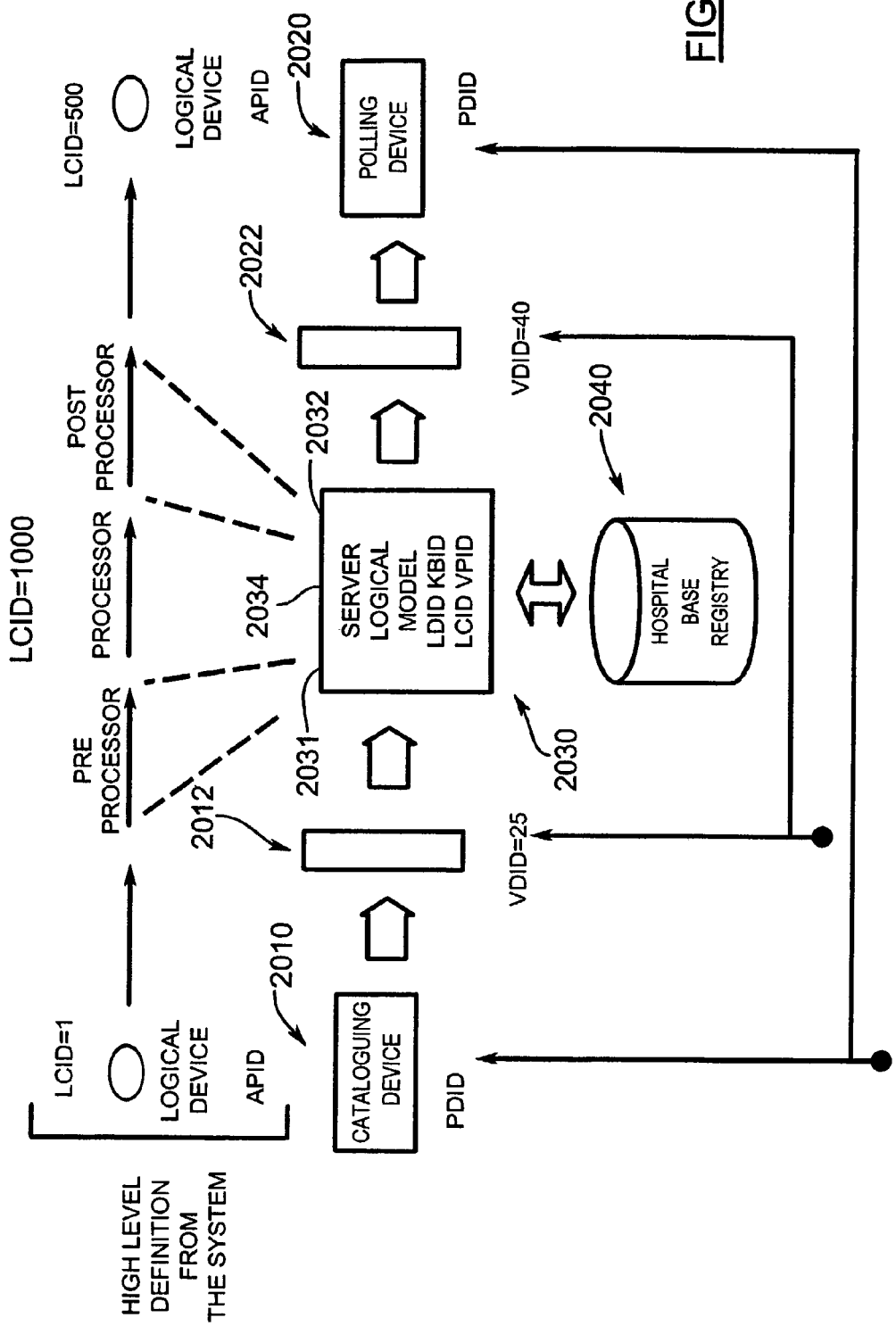
FIG. 20 shows a poling based server for auditing movement of personnel within a health care facility according to another aspect of the present invention.

Reference is next made to FIG. 20, which shows a logical model for auditing the movement of personnel within the facility 1001 utilizing the system 1200 according to the present invention. As depicted in FIG. 20, the logical model comprises a cataloguing device 2010, a poling device 2020, a first virtual device 2012, a second virtual device 2022 and a server logical model 2030. The server logical model 2030 comprises a first pre-processor 2031, a second pre-processor 2032 and a processor 2034. The first virtual device 2012 interfaces the cataloguing device 2010 to the first pre-processor 2031 and the processor 2034; and the second virtual device 2022 interfaces the poling device 2020 to the second pre-processor 2032 and the processor 2034. The processor 2034 has an interface for accessing and storing information from the hospital registry or database indicated by reference 2040. The cataloguing device 2010 comprises a component or module in the first network layer 1210 (FIG. 12) which provides a receiver or tracking function as described above. The poling device 2020 comprises a component or module in the second network layer 1220 (FIG. 12) which provides a supervisory or regulatory functions as described above.

According to an aspect of this logic model or architecture, the cataloguing device 2010 and/or the poling device 2020 may be located at a physical location or locations remote from the hospital registry 2040. In one implementation, the hospital registry or database 2040 is located at a central site. The virtual devices 2012 and 2022 comprise gateway network components (e.g. x0.25 TCP/IP devices) which interface the cataloguing device 2010 and/or the poling device 2020 over the Internet or other wide area network.

As shown in FIG. 20, the cataloguing device 2010 converts the signals received from the RFID tags 1240 (FIG. 12) into personal device identifiers or PDID's. The first virtual device 2012 converts the PDID into a virtual device identifier or VDID. The first virtual device 2012 passes the PDID to the server logical model 2030. The server logical model 2030 includes pre-processing and processing components for converting the PDID into a logical device identifier or LDID or LCID which is then stored in the hospital registry or database 2040. Similarly, the server logical model 2030 includes pre-processing and processing components for retrieving the logical device identifier (i.e. the LDID or LCID) from the registry or database 2040 and converting the logical device identifier LDID into an associated virtual device identifier or VDID by the second virtual device 2022. The virtual device identifier VDID is provided to the poling device 2020 for utilization in poling or supervisory functions, for example, as described above. As shown in FIG. 20, the server logical model 2030 also includes modules for a knowledge base identifier or KBID and a virtual processor identifier module or VPID.

The present invention may be embodied in other specific forms without departing from the spirit or essential characteristics thereof. Other adaptations and modifications of the invention will be obvious to those skilled in the art. Therefore, the presently discussed embodiments are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. A system for tracking and auditing the movement of persons in a facility, said system comprising:
    a first network having a plurality of passive receivers, each of said passive receivers having an input for receiving an identification signal, each of the persons in the facility having an associated identification signal, and each of said passive receivers including an output for outputting an output signal for each of said identification signals, each passive receiver having a scanning antenna installed around a perimeter of a passageway in the facility, the plurality of scanning antennas being located throughout the facility;
    a plurality of transmitters, each of the persons wearing one of said transmitters, and each of said transmitters transmitting the identification signal associated with the person;
    a controller having an input port for receiving the output signals, and including a component for generating a temporal record for each of the persons in response to the detection of said identification signal of the person by one or more of said passive receivers;
    a second network having a plurality of active transceivers, each of said active transceivers having a poling transmitter for transmitting a periodic poling request to said transmitters, and each of said active transceivers having a poling receiver for receiving identification signals in response to said poling requests; and
    said controller further including an interface for receiving said poled identification signals, and having a component for generating an audit record for each of said transmitters in response to said poling request.

2. The system as claimed in claim 1, wherein said transceiver comprises a Balun antenna, said Balun antenna having input and output port coupled to a network module having a communication interface for transmitting and receiving signals from said associated Balun antenna.

3. The system as claimed in claim 1, wherein said controller includes a component for reconciling identification signals associated with persons who have left the facility, and the absence of a poled identification signal in response to the poling request.

4. The system as claimed in claim 1, wherein said controller includes a component for monitoring identification signals associated with persons who randomly leave and enter the facility.

5. A system for tracking and auditing the movement of persons in a facility, said system comprising:

a first network having a plurality of receivers, each of said receivers having an input for receiving an identification signal, each of the persons in the facility having an associated identification signal, and each of said receivers including an output for outputting an output signal for each of said identification signals;

a plurality of transmitters, each of the persons wearing one of said transmitters, and each of said transmitters transmitting the identification signal associated with the person;

said plurality of receivers being located throughout the facility;

a controller having an input port for receiving the output signals, and including a component for generating a temporal record for each of the persons in response to the detection of said identification signal of the person by one or more of said receivers and having a component for reconciling identification signals associated with persons who have left the facility, and the absence of a poled identification signal in response to the poling request;

a second network having a plurality of transceivers, each of said transceivers having a poling transmitter for transmitting a poling request to said transmitters, and each of said transceivers having a poling receiver for receiving identification signals in response to said poling requests; and said controller further including an interface for receiving said poled identification signals, and having a component for generating an audit record for each of said transmitters in response to said poling request, wherein the component for reconciling identification signals further includes a component for monitoring persons who have left the facility and remain on call for a possible call to return to the facility.

6. A method for tracking and auditing the movement of persons in a facility, said method comprising the steps of:

assigning an identifier to each person having access to the facility, and providing each of said persons with a transmitter for transmitting the assigned identifier;

passively detecting transmission of the identifiers for said persons at locations in the facility using a first network of scanning antennas installed around perimeters of passageways in the facility so as to track movement of said persons;

establishing a record for each of said persons, each of said records including temporal data indicating time and date for detection of the identifier for said associated person;

storing said records and making said records available for retrieval;

actively poling said transmitters by sending one or more poling requests using a second network of active antennas located throughout the facility;

receiving at the active antennas identification signals from said transmitters in response to said poling request;

generating an audit record for said transmitters based on the identification signal received in response to said poling request.

7. The method as claimed in claim 6, further including the step of reconciling missing identification signals with persons who have left the facility.

8. The method as claimed in claim 6, further including the step of monitoring identification signals associated with persons who randomly leave and enter the facility.

9. A method for tracking and auditing the movement of persons in a facility, said method comprising the steps of:

assigning an identifier to each person having access to the facility, and providing each of said persons with a transmitter for transmitting the assigned identifier;

detecting transmission of the identifiers for said persons at one or more locations in the facility based on movement of said persons;

establishing a record for each of said persons, each of said records including temporal data indicating time and date for detection of the identifier for said associated person;

storing said records and making said records available for retrieval;

poling said transmitters by sending one or more poling requests to one or more of said transmitters;

receiving identification signals from said transmitters in response to said poling request;

generating an audit record for said transmitters based on the identification signal received in response to said poling request; and monitoring persons who have left the facility and remain on call for a possible call to return to the facility, said monitoring operation utilizing said poled identification signals.

10. The method as claimed in claim 6, wherein said transmitters are applied to apparatus in the facility for tracking and auditing movement of said apparatus.

11. The method as claimed in claim 10, further including the step of initiating an alarm condition for a person or apparatus which is non-responsive to one or more of said poling requests.

* * * * *